US008815152B2

(12) United States Patent
Burgess-Cassler et al.

(10) Patent No.: US 8,815,152 B2
(45) Date of Patent: Aug. 26, 2014

(54) DEVICE FOR RAPID DETERMINATION OF DISEASE-ASSOCIATED THIOL COMPOUNDS

(75) Inventors: Anthony Burgess-Cassler, Lexington, KY (US); Boyd E. Haley, Lexington, KY (US)

(73) Assignee: Alt Bioscience, LLC, Lexington, KY (US)

( * ) Notice: Subject to any disclaimer, the term of this patent is extended or adjusted under 35 U.S.C. 154(b) by 0 days.

(21) Appl. No.: 12/456,293

(22) Filed: Jun. 15, 2009

(65) Prior Publication Data

US 2009/0311142 A1 Dec. 17, 2009

Related U.S. Application Data

(60) Provisional application No. 61/131,973, filed on Jun. 13, 2008, provisional application No. 61/145,393, filed on Jan. 16, 2009, provisional application No. 61/160,142, filed on Mar. 13, 2009, provisional application No. 61/186,453, filed on Jun. 12, 2009.

(51) Int. Cl.
*G01N 21/77* (2006.01)
*G01N 21/00* (2006.01)

(52) U.S. Cl.
USPC .................. 422/50; 422/51; 422/68.1

(58) Field of Classification Search
CPC ................. G01N 21/77; G01N 21/00
USPC ....................... 422/56, 50, 51, 68.1
See application file for complete search history.

(56) References Cited

U.S. PATENT DOCUMENTS

| 3,119,668 A | 1/1964 | Ellman |
| 3,318,910 A | 5/1967 | Williams |
| 4,334,540 A | 6/1982 | Preti et al. |
| 4,414,414 A | 11/1983 | Novak |
| 4,578,357 A | 3/1986 | Melpolder |
| 5,093,475 A | 3/1992 | Carroll et al. |
| 5,187,105 A | 2/1993 | Albarella et al. |
| 5,330,898 A | 7/1994 | Bar-Or et al. |

(Continued)

FOREIGN PATENT DOCUMENTS

| JP | 57-148252 | 9/1982 |
| JP | 62-239055 | 10/1987 |

(Continued)

OTHER PUBLICATIONS

Patent Cooperation Treaty, International Search Report and Written Opinion of the International Search Authority, PCT/US09/047393, Oct. 30, 2009, 18 pages.

(Continued)

*Primary Examiner* — Christine T Mui
(74) *Attorney, Agent, or Firm* — Viksnins Harris & Padys PLLP

(57) ABSTRACT

Disclosed is a single-use disposable article for determining the concentration of thiol compounds in a sample of fluid, a single-use disposable test strip for determining the concentration of thiol compounds in a sample of a fluid from a mammalian subject, a single-use disposable test strip for determining the risk that a mammalian subject is suffering from a particular malady, and a description of how to make and use the article and test strips.

31 Claims, 30 Drawing Sheets
(14 of 30 Drawing Sheet(s) Filed in Color)

(56) References Cited

U.S. PATENT DOCUMENTS

| | | | |
|---|---|---|---|
| 5,556,743 A * | 9/1996 | Gibboni et al. | 435/4 |
| 5,910,447 A | 6/1999 | Lawrence et al. | |
| 6,007,999 A | 12/1999 | Clark | |
| 6,255,066 B1 | 7/2001 | Louderback | |
| 6,436,658 B1 | 8/2002 | Seman | |
| 7,041,469 B2 * | 5/2006 | Lawrence et al. | 435/23 |
| 7,290,668 B2 | 11/2007 | Ward et al. | |
| 7,723,118 B2 | 5/2010 | Pendergrass | |
| 2001/0056246 A1 | 12/2001 | Rodriguez-Fernandez et al. | |
| 2002/0102627 A1 | 8/2002 | Lorber | |
| 2002/0120406 A1 | 8/2002 | Lorber | |
| 2004/0029171 A1 | 2/2004 | Wagner et al. | |
| 2004/0076584 A1 * | 4/2004 | Pendergrass | 424/9.6 |
| 2007/0053849 A1 | 3/2007 | Doyle et al. | |
| 2007/0259332 A1 | 11/2007 | Pendergrass | |
| 2010/0291699 A1 | 11/2010 | Pendergrass | |

FOREIGN PATENT DOCUMENTS

| | | | |
|---|---|---|---|
| JP | 4-69570 | 3/1992 | |
| JP | 9-225322 | 9/1997 | |
| JP | 2004245818 | 9/2004 | |
| JP | 2005010167 | 1/2005 | |
| JP | 2005017272 | 1/2005 | |
| WO | WO 97/05482 | 2/1997 | |
| WO | WO 2006/094185 A2 | 9/2006 | |
| WO | WO 2006094185 A2 * | 9/2006 | G01N 33/52 |

OTHER PUBLICATIONS

Riener et al., "Quick measurement of protein sulfydryls with Ellman's reagent and with 4, 4'-dithiodipyridine", *Anal Bioanal Chem*, 373, 266-276, (2002).

Wikipedia, "Urine test strip", 5 pages, last modified Aug. 31, 2010, downloaded Nov. 4, 2010, available at http://en.wikipedia.org/wiki/Urine_test_strip.

Singh, et al., "Formation of N-Substituted 2-Iminothiolanes When Amino Groups in Proteins and Peptides Are Modified by 2-Iminothiolane", *Anal. Biochem.*, 236(1), 114-125, (1996).

Gergel, et al., "Interaction of Nitric Oxide with 2-Thio-5-nitrobenzoic Acid: Implications for the Determination of Free Sulfhydryl Groups by Ellman's Reagent", *Arch. Biohem. Biophys.*, 347(2), 282-288, (1997).

Lamster, et al., "The polyamines putrescine, spermidine and spermine in human gingival crevicular fluid", *Arch. Oral Biol.*, 32(5), 329-333, (1987).

King, et al., "Preparation of protein conjugates via intermolecular disulfide bond formation", *Biochemistry*, 17(8), 1499-1506, (1978).

Aboshama, et al., "Effect of Ultra-High-Temperature Steam Injection Processing on Sulfur-Containing Amino Acids in Milk", *J. Dairy Sci.*, 60(9), 1374-1378, (1977).

Augusteyn et al., "The Location of Sulphydryl Groups in α-Crystallin", *Biochimica et Biophysica Acta 915*, 132-139 (1987).

Mohler et al., "Structure of 2-Keto-3-Deoxy-6-Phosphogluconate Aldolase, IV. Structural Features Revealed by Treatment of Urea and Ellman's Reagent", *Archives of Biochemistry and Biophysics 151*, 251-260 (1972).

Tian et al., "Studies on the Reactivity of the Essential Sulfhyudryl Groups as a Conformational Probe for the Fatty Acid Synthetase of Chicken Liver", *Journal of Biological Chemistry*, vol. 260 (20), 11375-11387 (1985).

Meng Huan-xin, "Associate between periodontitis and diabetes mellitus", *Journal of Peking University( Health Sciences*, vol. 39, (1), 18-20 (2007). [English Abstract included.]

Feng, "Periodontitis is not just a matter of tooth", Digest of Science and Technology, 4, (2003). [English Summary included.].

Chinese Office Action for corresponding application No. 200980131587.7, 14 pages, Mar. 10, 2014.

\* cited by examiner

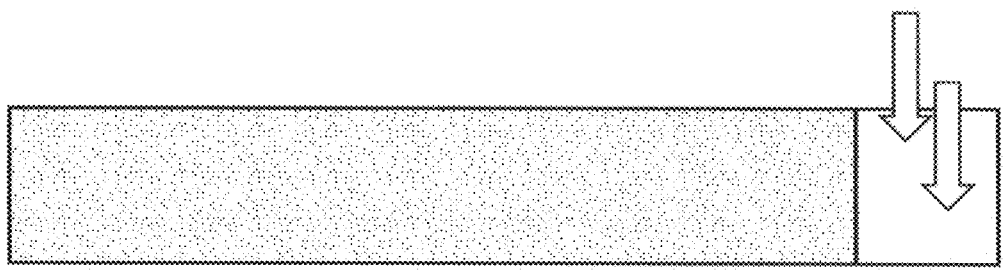
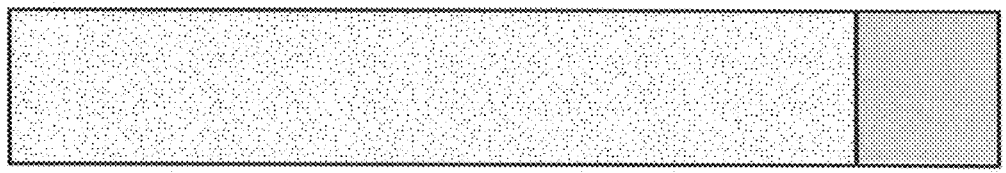
Fig. 1

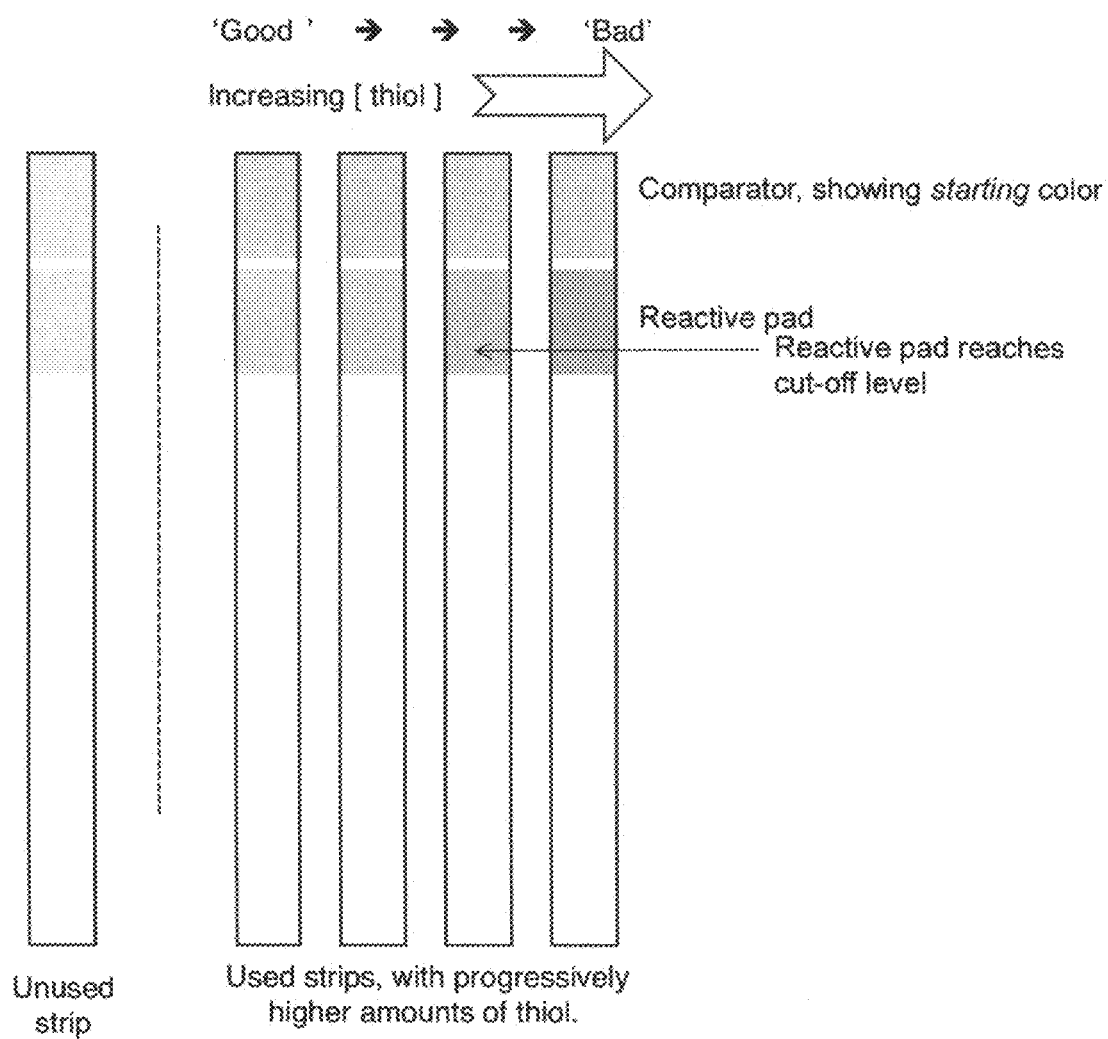

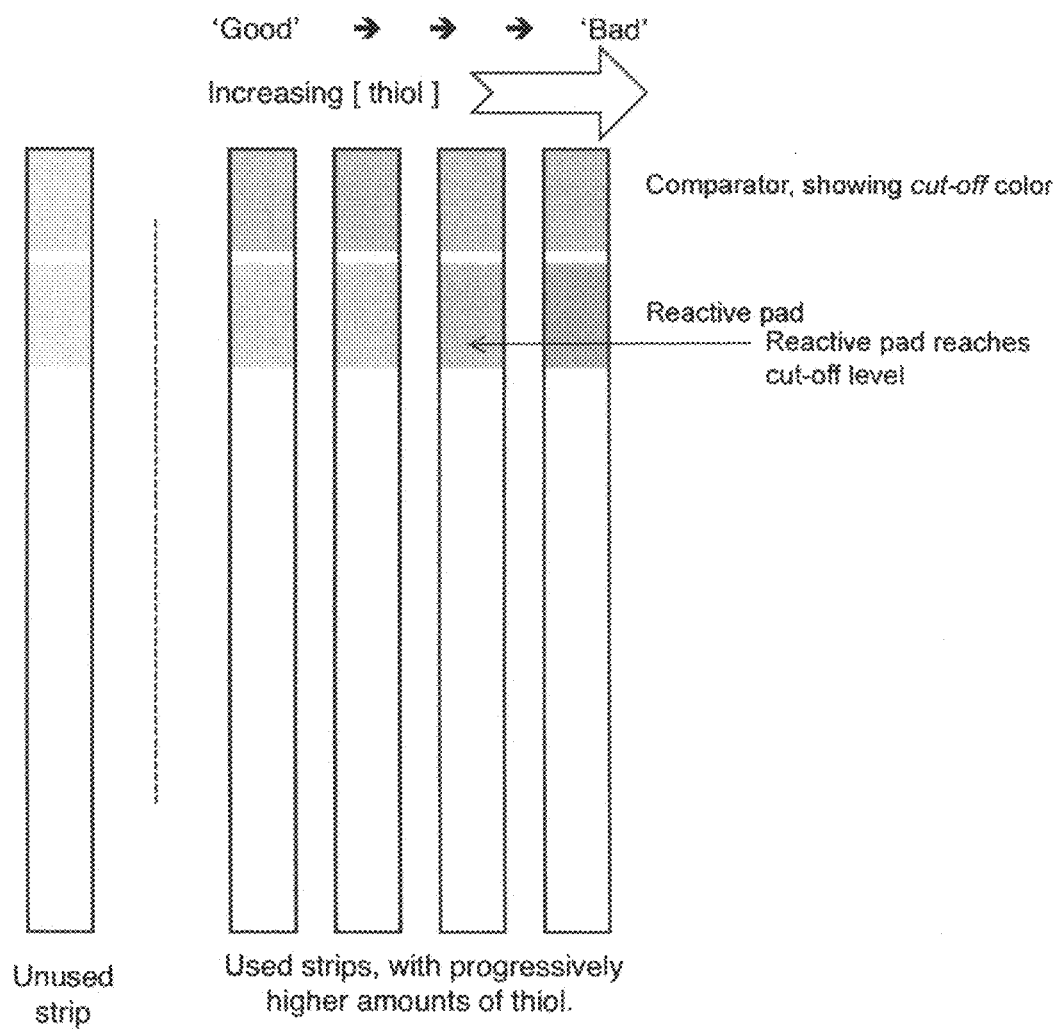

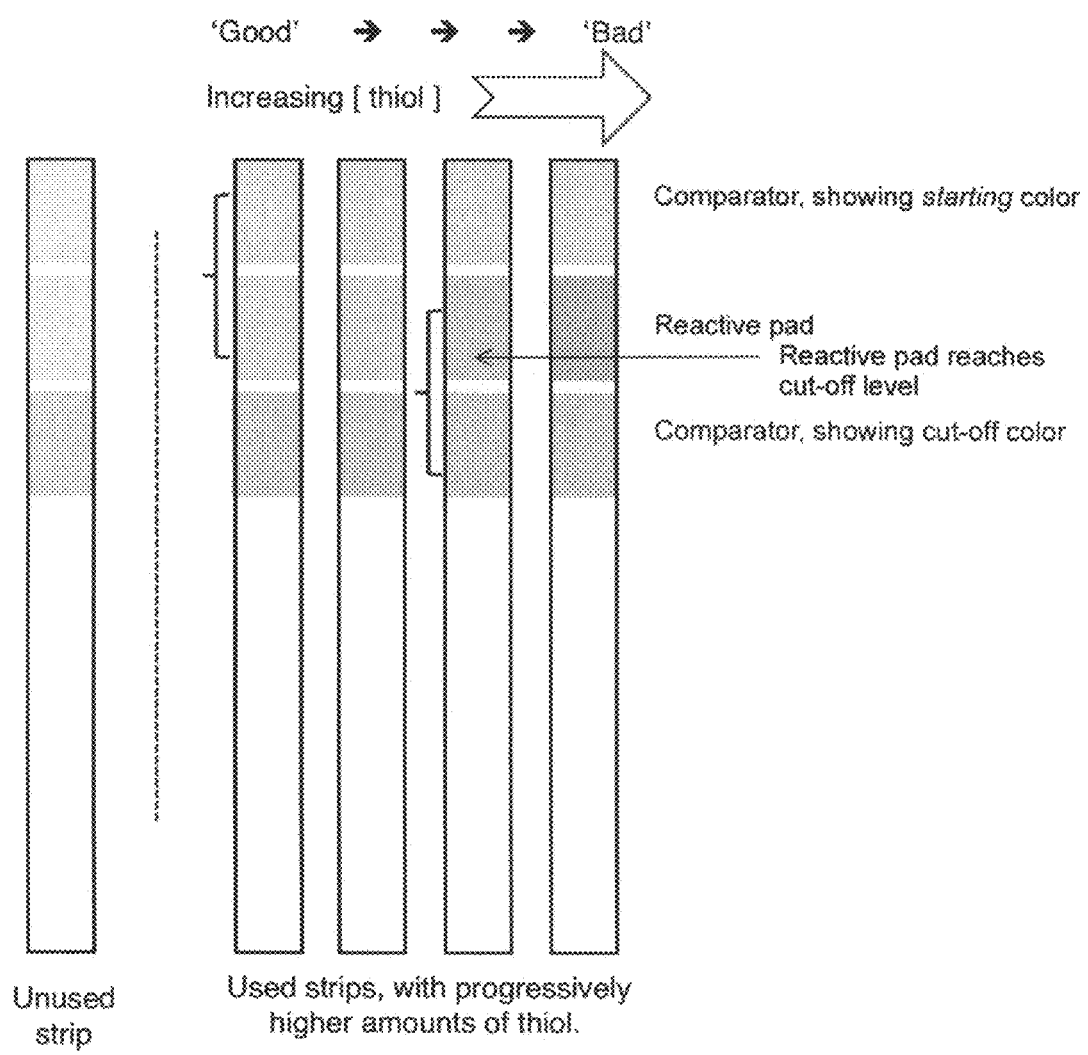

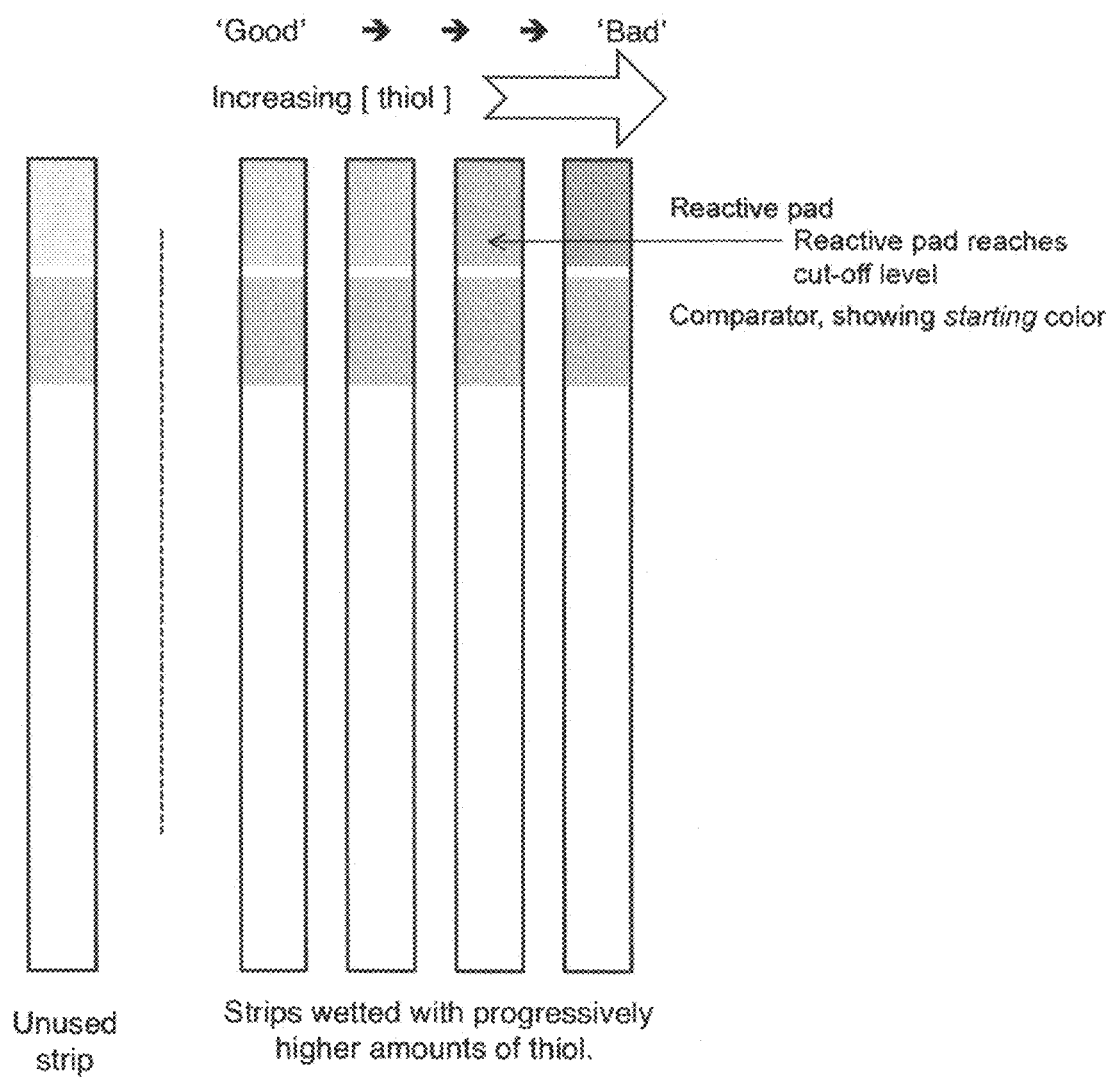

*Fig. 3A*
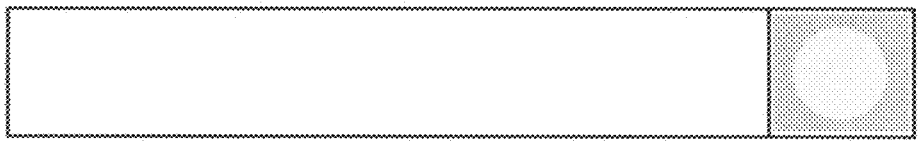
Unused strip or negative result
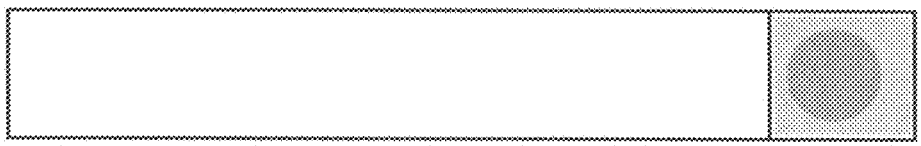
Positive result Fig. 3B
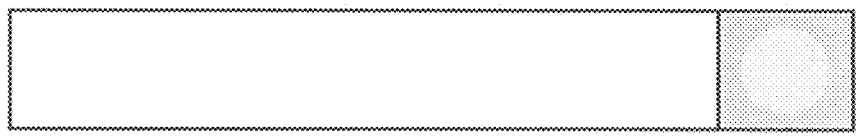
Unused strip or negative result
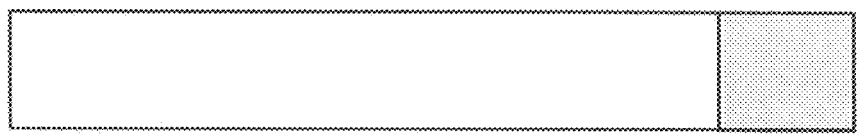
The two strips immediately above would both be considered positive

*Fig. 3C*
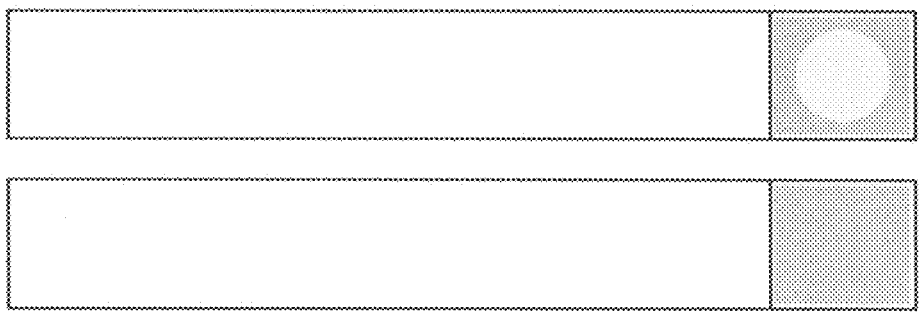
Both strips are negative
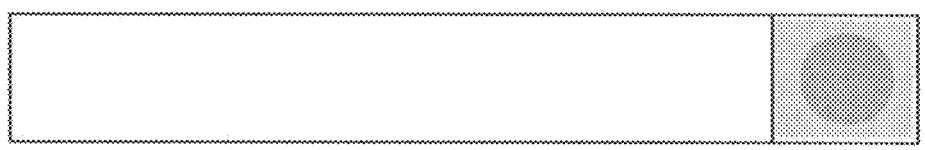
The strip shows a positive result Fig. 9D
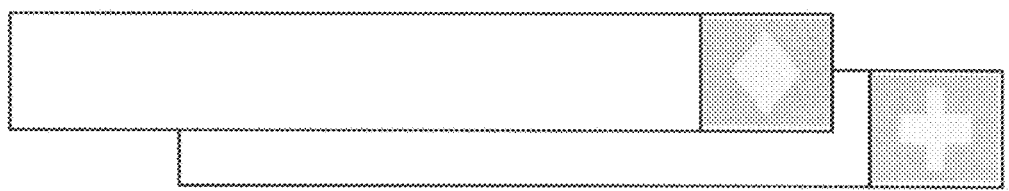
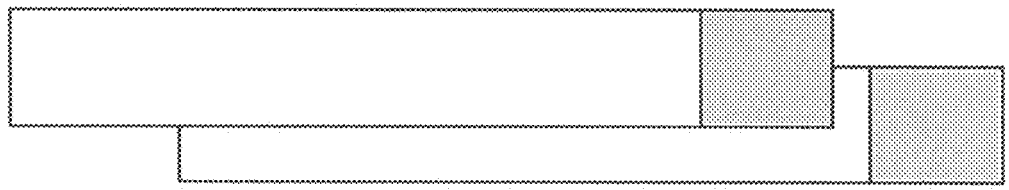
Negative or unused strips
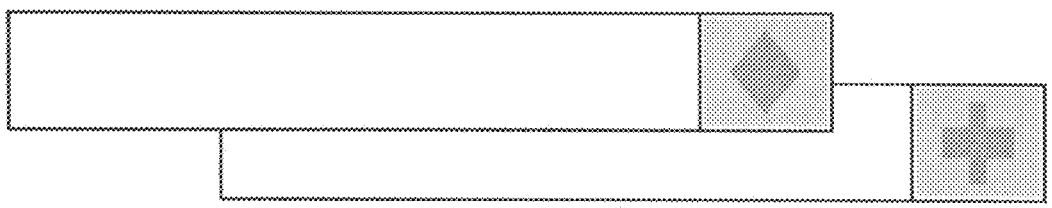
Positive result Fig. 9E
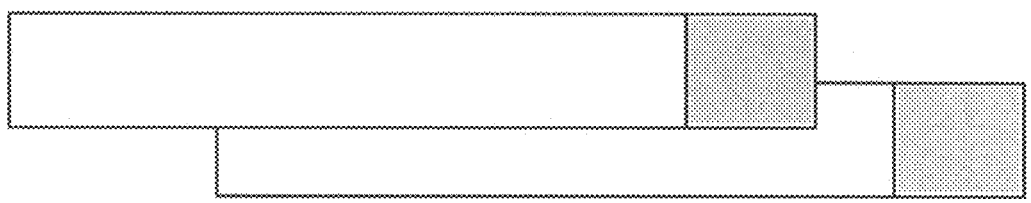
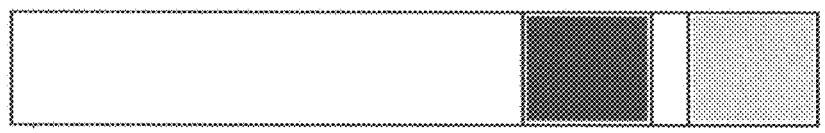
Unused strip or negative result
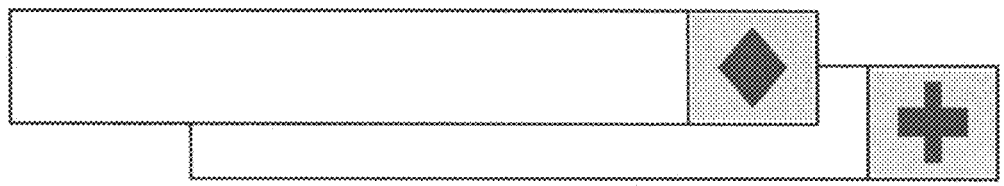
The three strips immediately above would both be considered positive

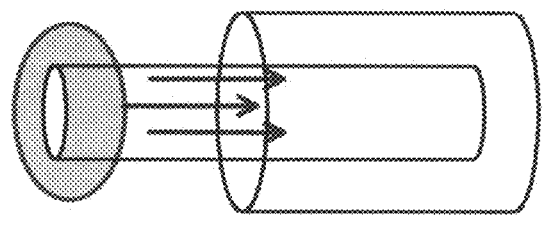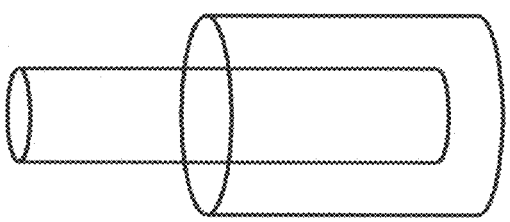
Fig. 4A

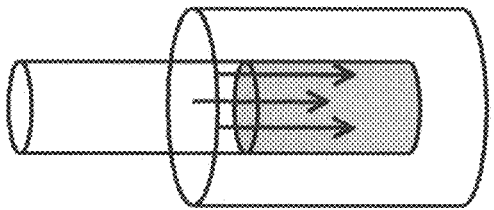
Apply sample & push cylinders together. fluid then migrates into reaction area
Yellow color develops in reagent cylinder
Use
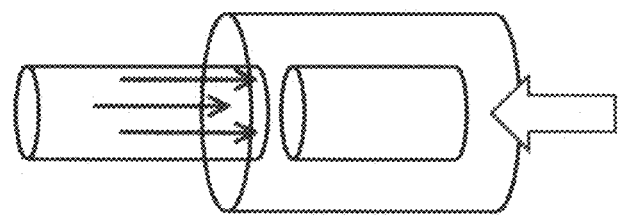
'Blank' cylinder
insert 2 cylinders into clear protective 'housing'
Manufacturing
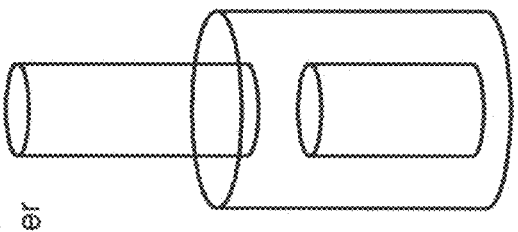
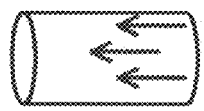
Apply reagent to one of two cylinders; dry
Fig. 4B

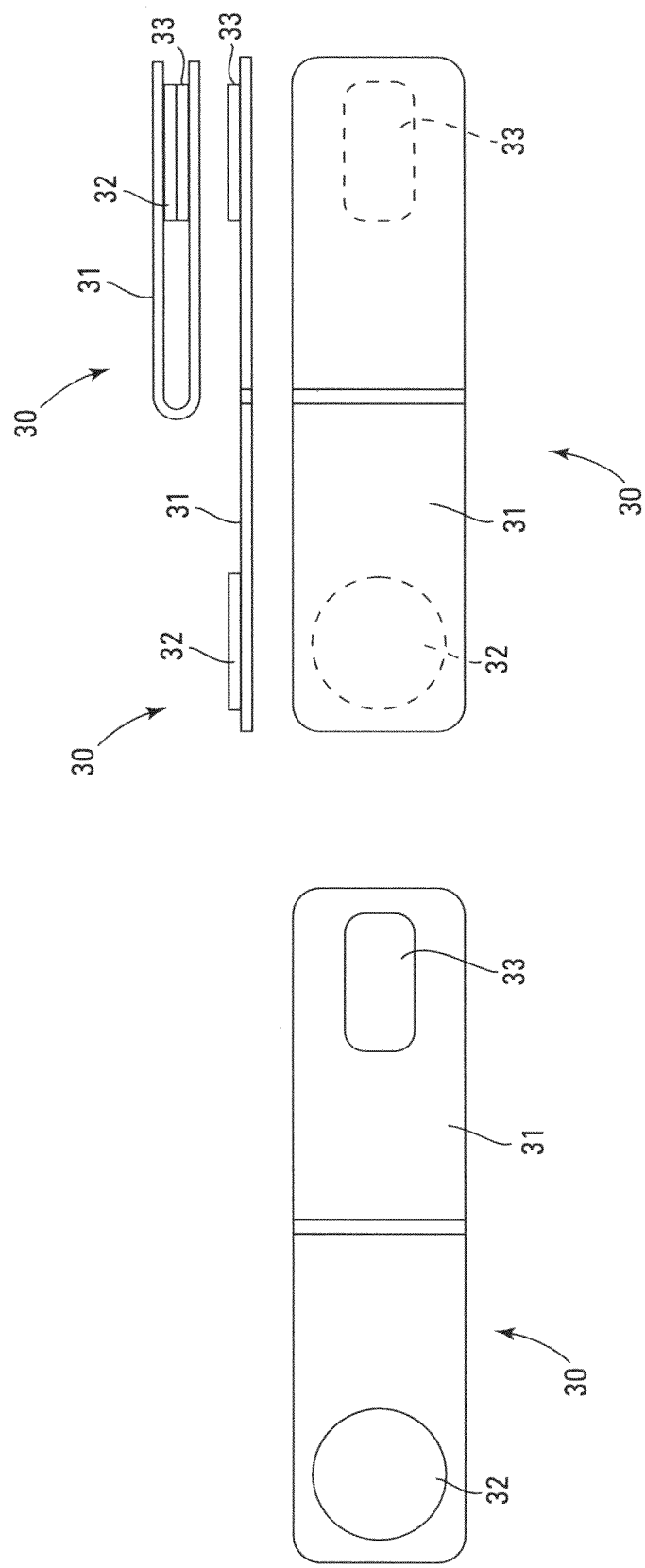

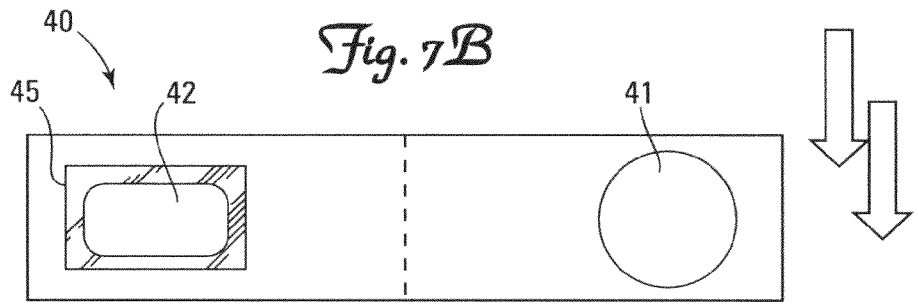
Stick, with 2 seperate pads; load sample at one end
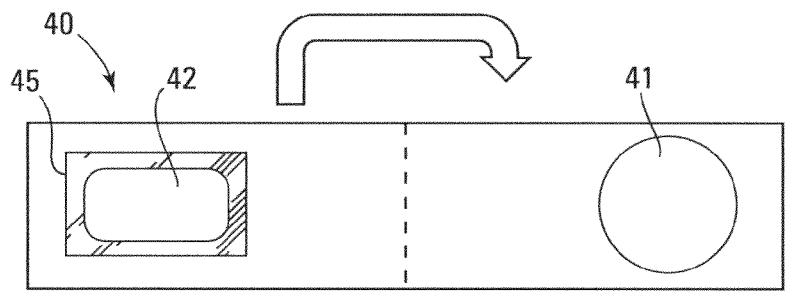
Fold, at score mark; squeeze pads together gently
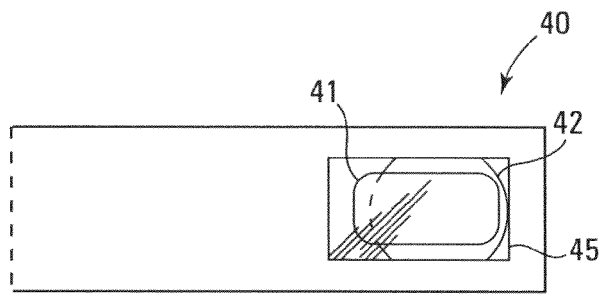
View result through back of reagent pad

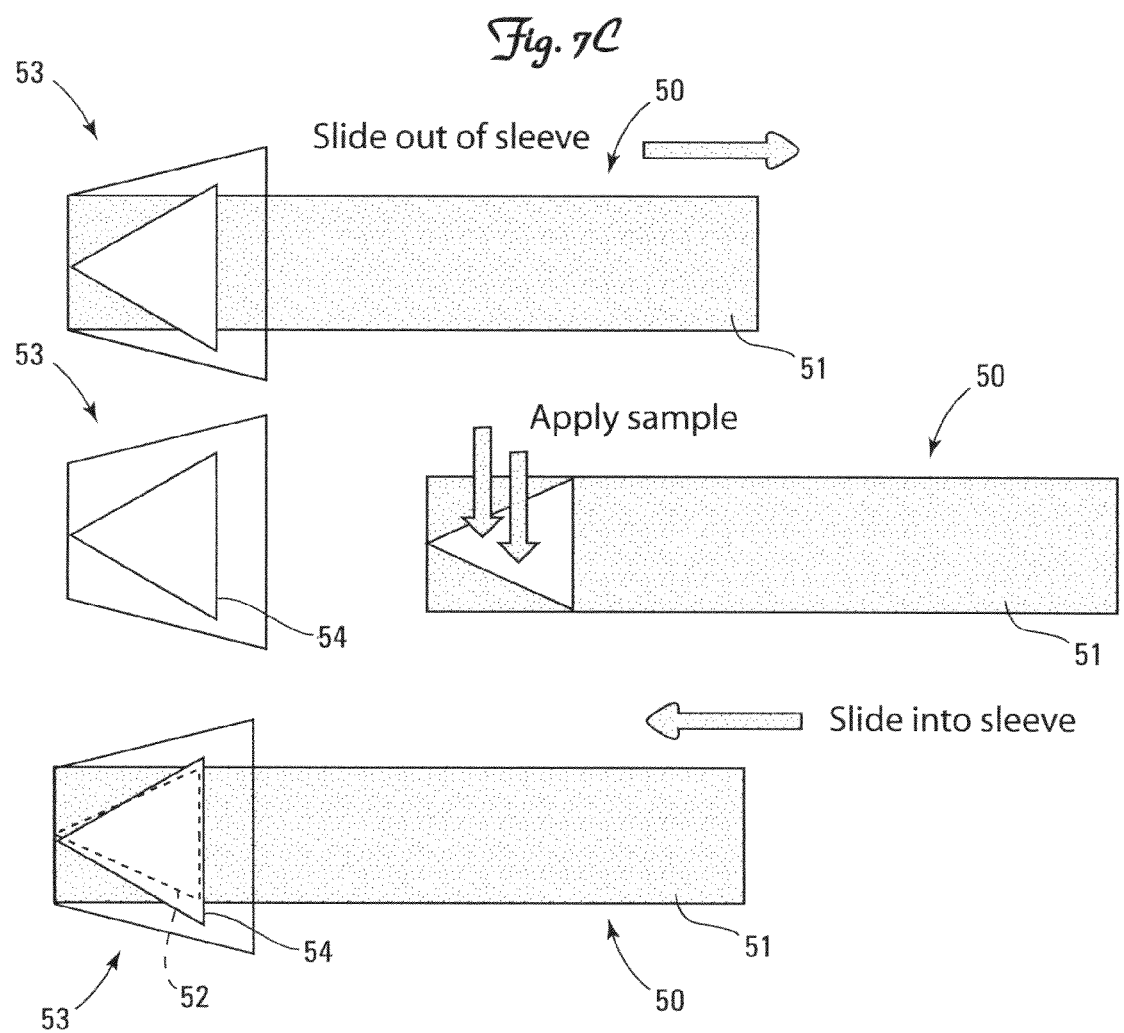

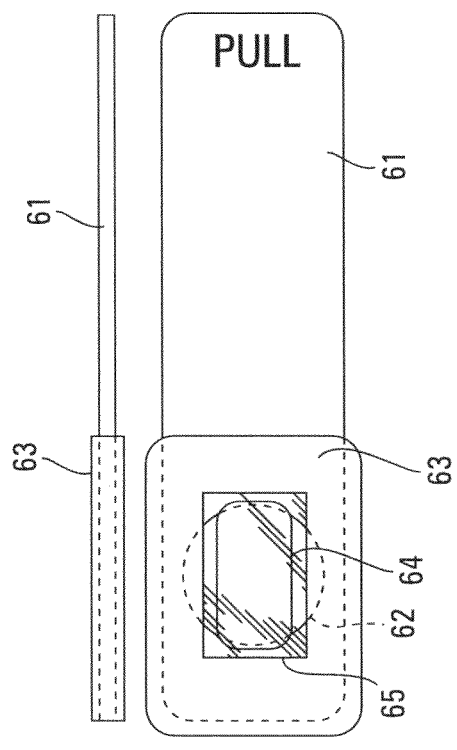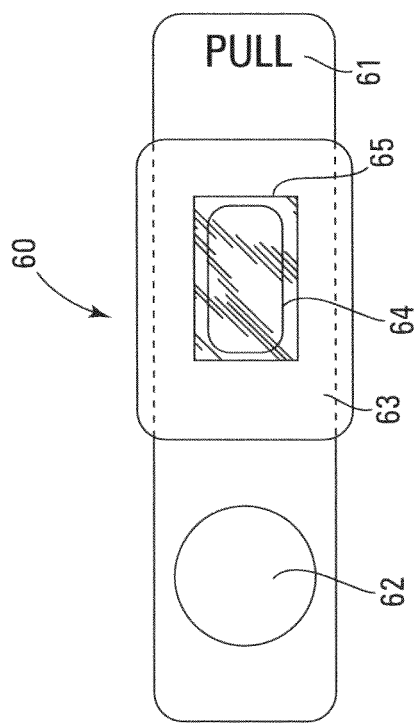
Fig. 7D

Fig. 8B
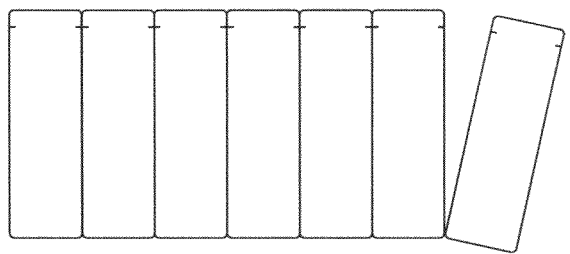
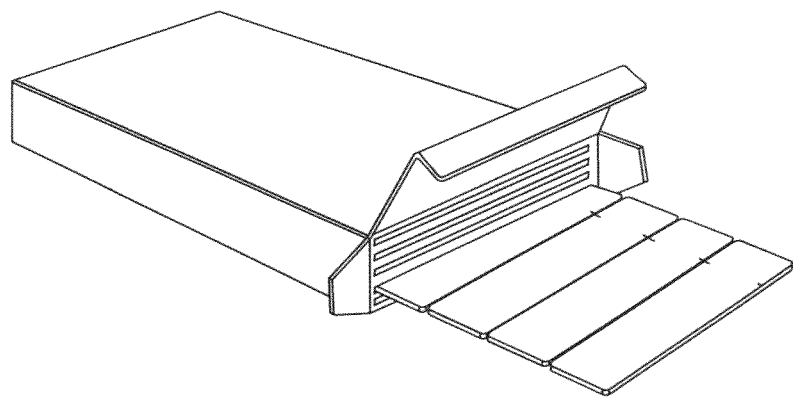

CALCULATION OF DEGRADATION RATES AT A GIVEN TEMPERATURE
BASED ON PRODUCT DEGRADATION AT HIGHER TEMPERATURES

WHERE PRODUCT WITH ACTIVATION ENERGY OF $E_a$ IS STORED AT TEMPERATURE T1 AND EXHIBITS A DEGRADATION RATE k1;
EXPECTED DEGRADATION RATE IS CALCULATED (k2) FOR WHEN PRODUCT IS STORED AT TEMPERATURE T2

REALISTIC ESTIMATE ($Q_{10}$=3)

GIVEN:
k1 = 1 SEC(-1)*
Ea = 18.7 KCAL/MOLE
R = 1.9871 CALORIES DEGREES K(-1) MOLE
T1 (°C) = 37 DEG. C         T1 (K) = 310 °K
T2 (°C) = 22 DEG. C         T2 (K) = 295 °K
THEN:
k2 = 0.21361 M(-1)SEC(-1)
WHICH MEANS
   88 DAY(S) AT    37 °C IS EQUIVALENT TO    411.96 DAYS OR
                                             13.53 MONTHS OR   } AT    22 °C
                                             1.128 YEARS $Q_{10}$ = 3.00

CONSERVATIVE ESTIMATE ($Q_{10}$= 2)

GIVEN:
k1 = 1 SEC(-1)*
Ea = 12.55 KCAL/MOLE
R = 1.9871 CALORIES DEGREES K(-1) MOLE
T1 (°C) = 37 DEG. C         T1 (K) = 310 DEG. K
T2 (°C) = 22 DEG. C         T2 (K) = 295 DEG. K
THEN:
k2 = 0.3549 M(-1)SEC(-1)
WHICH MEANS
   88 DAY(S) AT    37 °C IS EQUIVALENT TO    247.96 DAYS OR
                                             8.15 MONTHS OR    } AT    22 °C
                                             0.679 YEARS $Q_{10}$ = 2.00

BASED ON:
ln(k2/k1) = (-Ea/R)* ((1/T2) - (1/T1))

NOTE:
$E_a \approx 6.15(Q_{10}) + 0.25$

FIG. 14

DEVICE FOR RAPID DETERMINATION OF DISEASE-ASSOCIATED THIOL COMPOUNDS

RELATED APPLICATION

This patent application claims the benefits of priority of U.S. Application Ser. Nos. 61/131,973, filed Jun. 13, 2008, 61/145,393, filed Jan. 16, 2009, 61/160,142, filed Mar. 13, 2009 and 61/186,453, filed Jun. 12, 2009, which applications are herein incorporated by references.

STATEMENT REGARDING FEDERALLY SPONSORED RESEARCH & DEVELOPMENT

The invention described in this application was not made pursuant to any federally sponsored research or development.

BACKGROUND OF THE INVENTION

Until very recently, the intimate connection between oral and systemic health has been poorly understood and largely ignored. However, a formidable body of evidence now makes clear that oral maladies such as periodontitis are closely associated with disorders affecting the whole body, such as cardiovascular disease, Type II diabetes, and preterm delivery.

BRIEF SUMMARY OF THE INVENTION

Diagnosis of periodontitis has been and remains a laborious process in which the space in the periodontal pocket surrounding each tooth must be probed multiple times while the patient sits for a prolonged interval in the dentist's chair. The time and discomfort involved in traditional diagnostic procedures have deterred patients and led to an overall underdiagnosis of this serious but treatable condition.

Periodontitis involves both microbial infection of host tissue and the host's inflammatory response. While analytically separable, these two aspects in reality operate in tandem to exact a toll of tissue destruction over the course of years and indeed decades.

When viewed from such a long-term perspective, periodontitis can be seen to be part of a continuum in which the level of certain microbes gradually increases, often in conjunction with increased inflammation. In this way, the progression from halitosis, associated with what may appear at the time to be benign microbial overgrowth, through gingivitis and on to periodontitis, shows characteristics of a positive-feedback loop that can in principle be interrupted through appropriate prophylaxis and/or therapeutic intervention.

One distinctive biochemical characteristic of this destructive spiral is an increase in the level of thiol compounds in certain oral fluids as the subject progresses from halitosis to gingivitis to periodontitis. Thiol compounds are those bearing an —SH or sulfhydryl functional group and are considered also to include sulfide anion ($HS^-$) as well as compounds bearing a thiolate anion ($RS^-$).

Measurement of thiol compounds in oral fluids has typically involved complicated apparatus replete with electrical circuitry or multi-step, multi-container, time-consuming assays. Accordingly, there has been a long-felt need for a simple, quick and cost-effective way to measure thiol compounds in oral fluids.

The present invention fulfills this long-felt need and incidentally addresses the more general problem of rapid and convenient determination of thiol levels in fluids and the more specific problem of rapid and convenient assessment of a subject's risk of various conditions and/or maladies.

The invention provides a single-use disposable article for determining the concentration of thiol compounds in a sample of fluid.

BRIEF DESCRIPTION OF THE FIGURES

This patent or application file contains at least one drawing executed in color. Copies of this patent or patent application publication with color drawing(s) will be provided by the U.S. Patent and Trademark Office upon request and payment of the necessary fee.

FIG. 1 depicts a direct contact method. The figure depicts two test strips. The upper one is a test strip with a pad impregnated with reagent solution. Arrows depict the application of a test sample. The bottom one depicts the test strip after a period of time, where the pad develops color after oral fluid (e.g., tongue contact) enters the pad, and reacts with the reagent to impart a color change to the pad.

FIGS. 2A-2D depict a direct contact method.

FIGS. 3A-3E depict alternative test strip configurations.

FIGS. 4A and 4B depict indirect contact devices (proximal/distal type).

FIGS. 7A-7D depict various embodiments of indirect contact devices, wherein folding or sliding brings separated components into contact with one another.

FIGS. 8A-8F depict various packaging designs for the present invention.

FIG. 14 provides the calculation of degradation rates as a given temperature based on product degradation at higher temperatures.

DETAILED DESCRIPTION OF THE INVENTION

Figure 5:
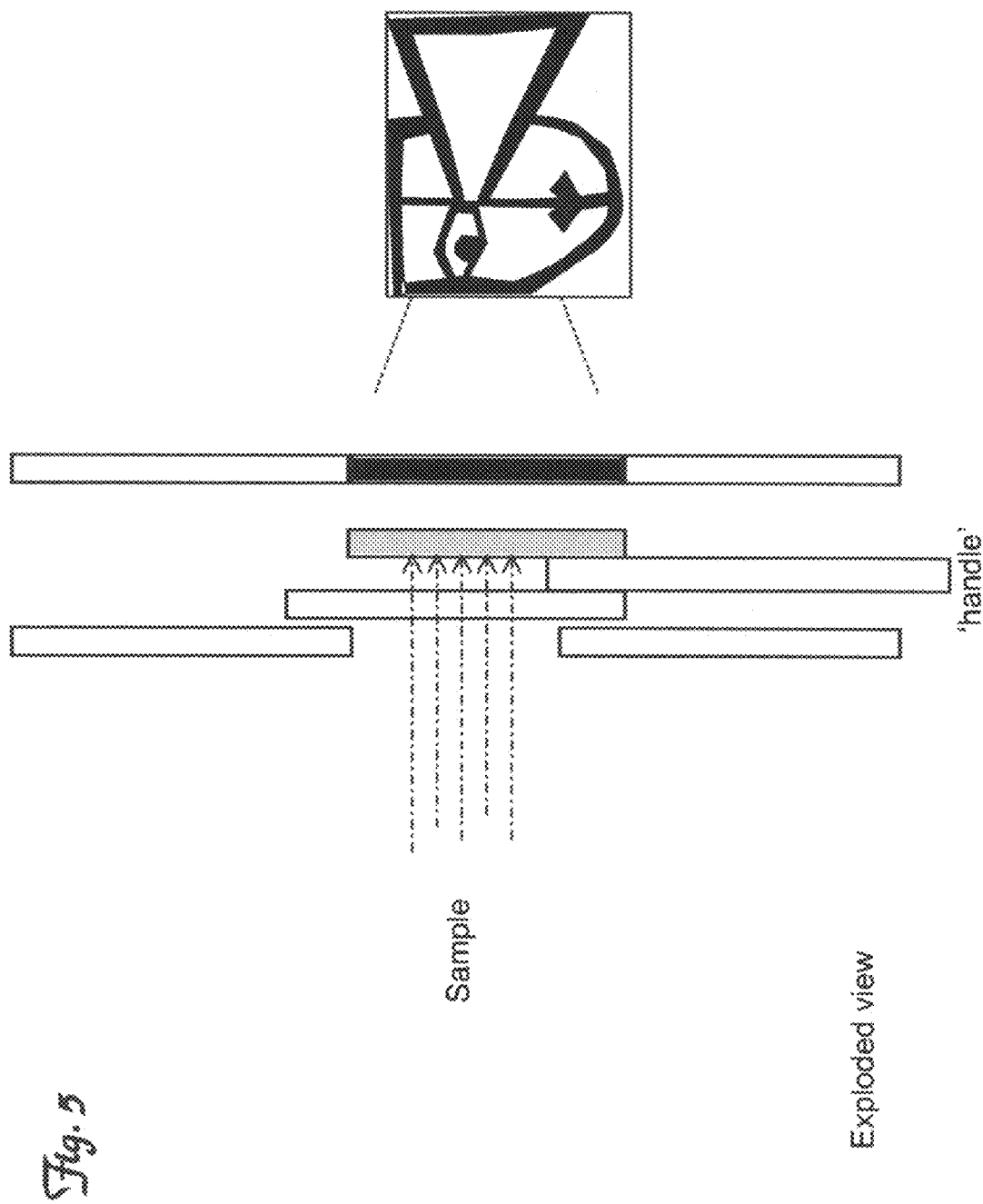
FIG. 5 depicts an example of an indirect contact device (Masked type).

The invention provides a single-use disposable article for determining the concentration of thiol compounds in a sample of fluid.

The following detailed description of the invention is intended to be understood by a person skilled in the diagnostic test strip and chemical arts. Accordingly, the terms employed in the detailed description are intended in general to have their ordinary meaning in the diagnostic test strip and chemical arts. Where the terms employed have no ordinary meaning that is peculiar to those arts, the terms are intended to have their ordinary meaning within contemporary American English usage, where that usage is intended to have a lasting legal effect. If any term is defined or clarified within the text of the present document, the definition or clarification within the text of the present document is intended to control over any other meaning of the term.

When used in connection with the invention, each of "5,5'-dithiobis-(2-nitrobenzoic acid)," "5-(2-aminoethyl)-dithio-2-nitrobenzoic acid," "N,N'-bis(4-nitrobenzylidene)-4,4'-dithiodianiline," "N,N'-bis(3-nitrobenzylidene)-4,4'-dithiodianiline," "N,N'-bis(2-nitrobenzylidene)-4,4'-dithiodianiline," "N,N'-bis(2,4-dinitrobenzylidene)-4,4'- dithiodianiline," and "N,N'-bis(4-nitrocinnamalylidene)-4,4'-dithiodianiline" refers not only to the respective composition itself but also to any of its salts, including any of its cosmetically and/or pharmaceutically acceptable salts.

When used in connection with the invention, "absorbent material" refers to a fiber material. In certain embodiments, the absorbent material is a synthetic, biocompatible, non-woven and or porous/material. An absorbent material may be, for example, a fiber material comprising a polyamide. It is believed that an absorbent material may be a material such as is described in U.S. Pat. No. 7,290,668. An absorbent material may be a TRANSORB® brand material (TRANSORB is a registered trademark of Filtrona Richmond, Inc.) such as a TRANSORB® brand material designated R-27378 or R28445 D#4345 and available from Filtrona Fibertec, Richmond, Va., US.

When used in connection with the invention, "fluid" refers to a material at least a substantial portion of which can undergo flow. Gases and liquids are fluids. A fluid need not be homogeneous but may contain adventitious particulate or other extraneous matter. Accordingly, each of saliva, gingival crevicular fluid, gumline biofilm, tongue biofilm, tongue scrapings, and breath is a fluid, as is a mixture composed of any plurality of these, although any of these may contain some solids.

When used in connection with the invention, "matrix" refers to a portion or component of an article according to the invention on which and/or in which a sample may be collected and does not refer to a fluid that is sampled and does not refer to an analyte in that fluid.

When used in connection with the invention, "swatch" denotes a representative specimen of a color.

The invention is provided in numerous embodiments and can be discerned, inter alia, in various aspects. The following aspects provide an illustrative but non-limiting description of the breadth and applicability of the invention. The invention provides each of the following aspects:

Aspect 1. A single-use disposable article for determining the concentration of thiol compounds in a sample of fluid, the article comprising:
  (a) a matrix comprising at least one absorbent material, the matrix being capable of absorbing the sample; and
  (b) an amount of a detection reagent, the amount of the detection reagent being capable of providing, during a period of time after at least a portion of the amount of the detection reagent has been contacted with at least a portion of the sample, a signal indicating the concentration of thiol compounds in the sample.

Aspect 2. The article of aspect 1, wherein the article is a test strip.

Aspect 3. The article of aspect 1, wherein the sample of fluid is a sample of a physiological fluid.

Aspect 4. The article of aspect 3, wherein the physiological fluid is an oral fluid.

Aspect 5. The article of aspect 4, wherein the oral fluid comprises saliva and/or gingival crevicular fluid and/or gumline biofilm and/or tongue biofilm and/or tongue scrapings and/or breath.

Aspect 6. The article of aspect 1, wherein the at least one absorbent material comprises a polyamide material.

Aspect 7. The article of aspect 1, wherein the detection reagent comprises at least one of: 5,5'-dithiobis-(2-nitrobenzoic acid); 5-(2-aminoethyl)-dithio-2-nitrobenzoic acid; N,N'-bis(4-nitrobenzylidene)-4,4'-dithiodianiline; N,N'-bis(3-nitrobenzylidene)-4,4'-dithiodianiline; N,N'-bis(2-nitrobenzylidene)-4,4'-dithiodianiline; N,N'-bis(2,4-dinitrobenzylidene)-4,4'-dithiodianiline; N,N'-bis(4-nitrocinnamalylidene)-4,4'-dithiodianiline.

Aspect 8. The article of aspect 7, wherein the detection reagent is 5,5'-dithiobis-(2-nitrobenzoic acid).

Aspect 9. The article of aspect 1, wherein the period of time begins about one second after the at least a portion of the amount of the detection reagent has been contacted with the at least a portion of the sample and ends about ten minutes after the at least a portion of the amount of the detection reagent has been contacted with the at least a portion of the sample.

Aspect 10. The article of aspect 1, wherein the period of time begins about five seconds after the at least a portion of the amount of the detection reagent has been contacted with the at least a portion of the sample and ends about five minutes after the at least a portion of the amount of the detection reagent has been contacted with the at least a portion of the sample.

Aspect 11. The article of aspect 1, wherein the signal comprises an electromagnetic signal.

Aspect 12. The article of aspect 11, wherein the electromagnetic signal comprises a visible signal.

Aspect 13. A method for determining the concentration of thiol compounds in a sample of fluid, the method comprising:
  (a) providing a single-use disposable article comprising (i) a matrix comprising at least one absorbent material, the matrix being capable of absorbing the sample and (ii) an amount of a detection reagent, the amount of the detection reagent being capable of providing, during a period of time after at least a portion of the amount of the detection reagent has been contacted with at least a portion of the sample, a signal indicating the concentration of thiol compounds in the sample;
  (b) contacting the matrix with the sample;
  (c) observing the signal provided by the amount of the detection reagent;
  (d) comparing the signal provided by the amount of the detection reagent to one or more reference values, each of which reference values is indicative of a concentration of thiol compounds, thereby determining the concentration of thiol compounds in the sample.

Aspect 14. The method of aspect 13, wherein the fluid is a physiological fluid.

Aspect 15. The method of aspect 14, wherein the physiological fluid is an oral fluid.

Aspect 16. The method of aspect 15, wherein the oral fluid comprises saliva and/or gingival crevicular fluid and/or gumline biofilm and/or tongue biofilm and/or tongue scrapings and/or breath.

Aspect 17. The method of aspect 13, wherein the article is a test strip.

Aspect 18. The method of aspect 13, wherein the at least one absorbent material comprises a polyamide material.

Aspect 19. The method of aspect 13, wherein the detection reagent comprises at least one of: 5,5'-dithiobis-(2-nitrobenzoic acid), also known as DTNB; 5-(2-aminoethyl)-dithio-2-nitrobenzoic acid; N,N'-bis(4-nitrobenzylidene)-4,4'-dithiodianiline; N,N'-bis(3-nitrobenzylidene)-4,4'-dithiodianiline; N,N'-bis(2-nitrobenzylidene)-4,4'-dithiodianiline; N,N'-bis(2,4-dinitrobenzylidene)-4,4'-dithiodianiline; N,N'-bis(4-nitrocinnamalylidene)-4,4'-dithiodianiline.

Aspect 20. The method of aspect 19, wherein the detection reagent is 5,5'-dithiobis-(2-nitrobenzoic acid).

Aspect 21. The method of aspect 13, wherein the period of time begins about one second after the at least a portion of the amount of the detection reagent has been contacted with the at least a portion of the sample and ends about ten minutes after the at least a portion of the amount of the detection reagent has been contacted with the at least a portion of the sample.

Aspect 22. The method of aspect 13, wherein the period of time begins about five seconds after the at least a portion of the amount of the detection reagent has been contacted with the at least a portion of the sample and ends about five minutes after the at least a portion of the amount of the detection reagent has been contacted with the at least a portion of the sample.

Aspect 23. The method of aspect 13, wherein the signal comprises an electromagnetic signal.

Aspect 24. The method of aspect 23, wherein the electromagnetic signal comprises a visible signal.

Aspect 25. The method of aspect 24, wherein each of the one or more reference values is provided as a paired combination of (a) a swatch of color and (b) a concentration of thiol compounds.

Aspect 26. A method for determining the risk that a mammalian subject is suffering from a particular malady, the method comprising:
  (a) providing a single-use disposable article comprising (i) a matrix comprising at least one absorbent material, the matrix being capable of absorbing the sample and (ii) an amount of a detection reagent, the amount of the detection reagent being capable of providing, during a period of time after at least a portion of the amount of the detection reagent has been contacted with at least a portion of the sample, a signal indicating the concentration of thiol compounds in the sample;
  (b) contacting the matrix with a sample comprising one or more physiological fluids from the subject;
  (c) observing the signal provided by the amount of the detection reagent;
  (d) comparing the signal provided by the amount of the detection reagent to one or more reference values, each of which reference values is indicative of a risk that a subject is suffering from the particular malady,
thereby determining the risk that the subject is suffering from the particular malady.

Aspect 27. The method of aspect 26, wherein the fluid is a physiological fluid.

Aspect 28. The method of aspect 27, wherein the physiological fluid is an oral fluid.

Aspect 29. The method of aspect 28, wherein the oral fluid comprises saliva and/or gingival crevicular fluid and/or gumline biofilm and/or tongue biofilm and/or tongue scrapings and/or breath.

Aspect 30. The method of aspect 26, wherein the article is a test strip.

Aspect 31. The method of aspect 26, wherein the at least one absorbent material comprises a polyamide material.

Aspect 32. The method of aspect 26, wherein the detection reagent comprises at least one of: 5,5'-dithiobis-(2-nitrobenzoic acid); 5-(2-aminoethyl)-dithio-2-nitrobenzoic acid; N,N'-bis(4-nitrobenzylidene)-4,4'-dithiodianiline; N,N'-bis(3-nitrobenzylidene)-4,4'-dithiodianiline; N,N'-bis(2-nitrobenzylidene)-4,4'-dithiodianiline; N,N'-bis(2,4-dinitrobenzylidene)-4,4'-dithiodianiline; N,N'-bis(4-nitrocinnamalylidene)-4,4'-dithiodianiline.

Aspect 33. The method of aspect 32, wherein the detection reagent is 5,5'-dithiobis-(2-nitrobenzoic acid).

Aspect 34. The method of aspect 26, wherein the period of time begins about one second after the at least a portion of the amount of the detection reagent has been contacted with the at least a portion of the sample and ends about ten minutes after the at least a portion of the amount of the detection reagent has been contacted with the at least a portion of the sample.

Aspect 35. The method of aspect 26, wherein the period of time begins about five seconds after the at least a portion of the amount of the detection reagent has been contacted with the at least a portion of the sample and ends about five minutes after the at least a portion of the amount of the detection reagent has been contacted with the at least a portion of the sample.

Aspect 36. The method of aspect 26, wherein the signal comprises an electromagnetic signal.

Aspect 37. The method of aspect 36, wherein the electromagnetic signal comprises a visible signal.

Aspect 38. The method of aspect 37, wherein each of the one or more reference values is provided as a paired combination of (a) a swatch of color and (b) a risk that a subject is suffering from the particular malady.

Aspect 39. The method of aspect 23, wherein at least one of the steps of observing and/or comparing is performed by an automated reader.

Aspect 40. The method of aspect 36, wherein at least one of the steps of observing and/or comparing is performed by an automated reader.

Aspect 41. The method of aspect 38, wherein the particular malady is periodontitis.

Aspect 42. The method of aspect 38, wherein the particular malady is gingivitis.

Aspect 43. The method of aspect 38, wherein the particular malady is halitosis.

Aspect 44. The method of aspect 38, wherein the particular malady is cardiovascular disease.

Aspect 45. The method of aspect 38, wherein the particular malady is Type II diabetes.

Aspect 46. The method of aspect 38, wherein the particular malady is preterm delivery.

Aspect 47. A kit comprising:
  (a) at least one single-use disposable article for determining the concentration of thiol compounds in a sample of fluid, the article comprising:
    (i) a first matrix comprising at least one absorbent material, the matrix being capable of absorbing the sample; and
    (ii) an amount of a detection reagent, the amount of the detection reagent being capable of providing, during a period of time after at least a portion of the amount of the detection reagent has been contacted with at least a portion of the sample, a visible signal indicating the concentration of thiol compounds in the sample;
  (b) a comparator on which is printed and/or affixed:
    (i) at least one swatch of color against which to compare the visible signal; and
    (ii) in association with each swatch of color, an alphanumeric identifier indicating a relative concentration of thiol compounds associated with the swatch of color;
  (c) optionally packaging suitable for containing the article and the comparator;
  (d) optionally instructions for use of the article and the comparator.

Aspect 48. The article of aspect 12 further comprising a comparator region, the comparator region comprising at least one swatch of color against which to compare the visible signal.

Aspect 49. A single-use disposable test strip for determining the concentration of thiol compounds in a sample of a fluid from a mammalian subject, the test strip comprising:

(a) a matrix comprising at least one absorbent material, the matrix being capable of absorbing the sample; and (b) an amount of a detection reagent, the amount of the detection reagent being capable of providing, during a period of time after at least a portion of the amount of the detection reagent has been contacted with at least a portion of the sample, a signal indicating the concentration of thiol compounds in the sample.

Aspect 50. The test strip of aspect 49, wherein the fluid comprises saliva and/or gingival crevicular fluid and/or gumline biofilm and/or tongue biofilm and/or tongue scrapings and/or breath.

Aspect 51. The test strip of aspect 49, wherein the detection reagent comprises at least one of: 5,5'-dithiobis-(2-nitrobenzoic acid); 5-(2-aminoethyl)-dithio-2-nitrobenzoic acid; N,N'-bis(4-nitrobenzylidene)-4,4'-dithiodianiline; N,N'-bis(3-nitrobenzylidene)-4,4'-dithiodianiline; N,N'-bis(2-nitrobenzylidene)-4,4'-dithiodianiline; N,N'-bis(2,4-dinitrobenzylidene)-4,4'-dithiodianiline; N,N'-bis(4-nitrocinnamalylidene)-4,4'-dithiodianiline.

Aspect 52. The test strip of aspect 51, wherein the detection reagent is 5,5'-dithiobis-(2-nitrobenzoic acid).

Aspect 53. The test strip of aspect 49, wherein the period of time begins about one second after the at least a portion of the amount of the detection reagent has been contacted with the at least a portion of the sample and ends about ten minutes after the at least a portion of the amount of the detection reagent has been contacted with the at least a portion of the sample.

Aspect 54. The test strip of aspect 49, wherein the period of time begins about five seconds after the at least a portion of the amount of the detection reagent has been contacted with the at least a portion of the sample and ends about five minutes after the at least a portion of the amount of the detection reagent has been contacted with the at least a portion of the sample.

Aspect 55. The test strip of aspect 49, wherein the signal comprises an electromagnetic signal.

Aspect 56. The test strip of aspect 55, wherein the electromagnetic signal comprises a visible signal.

Aspect 57. A single-use disposable test strip for determining the risk that a mammalian subject is suffering from a particular malady, the test strip comprising:

(a) a matrix comprising at least one absorbent material, the matrix being capable of absorbing the sample; and (b) an amount of a detection reagent, the amount of the detection reagent being capable of providing, during a period of time after at least a portion of the amount of the detection reagent has been contacted with at least a portion of the sample, a signal indicating the risk that the subject is suffering from the particular malady, and wherein (i) the detection reagent comprises at least one of: 5,5'-dithiobis-(2-nitrobenzoic acid); 5-(2-aminoethyl)-dithio-2-nitrobenzoic acid; N,N'-bis (4-nitrobenzylidene)-4,4'-dithiodianiline; N,N'-bis(3-nitrobenzylidene)-4,4'-dithiodianiline; N,N'-bis(2-nitrobenzylidene)-4,4'-dithiodianiline; N,N'-bis(2,4-dinitrobenzylidene)-4,4'-dithiodianiline; N,N'-bis(4-nitrocinnamalylidene)-4,4'-dithiodianiline; and (ii) the particular malady is at least one of: periodontitis, gingivitis, halitosis, cardiovascular disease, type II diabetes, preterm delivery.

Aspect 58. The test strip of aspect 57, wherein the detection reagent comprises 5,5'-dithiobis-(2-nitrobenzoic acid).

Aspect 59. The test strip of aspect 57, wherein the particular malady is periodontitis.

Aspect 60. The test strip of aspect 57, wherein the particular malady is gingivitis.

Aspect 61. The test strip of aspect 57, wherein the particular malady is halitosis.

Aspect 62. The test strip of aspect 57, wherein the particular malady is cardiovascular disease.

Aspect 63. The test strip of aspect 57, wherein the particular malady is type II diabetes.

Aspect 64. The test strip of aspect 57, wherein the particular malady is preterm delivery.

Aspect 65. A reagent solution comprising: a buffer, 5,5'-Dithiobis(2-nitrobenzoic acid) (DTNB), and a humectant.

Aspect 66. The reagent solution of aspect 65, wherein the buffer is a sodium phosphate buffer at a concentration of about 5 mM to 200 mM.

Aspect 67. The reagent solution of aspect 65, wherein the buffer is a sodium phosphate buffer at a concentration of about 20 mM to 150 mM.

Aspect 68. The reagent solution of aspect 65, wherein the buffer is a sodium phosphate buffer at a concentration of about 100 mM.

Aspect 69. The reagent solution of aspect 65, wherein the buffer is at a pH of about 6.5 to 8.5.

Aspect 70. The reagent solution of aspect 65, wherein the buffer is at a pH of about 6.5 to 7.5.

Aspect 71. The reagent solution of aspect 65, wherein the buffer is at a pH of about 7.0.

Aspect 72. The reagent solution of aspect 65, wherein the DTNB is present at a concentration of about 10 mg/L to 150 mg/L.

Aspect 73. The reagent solution of aspect 65, wherein the DTNB is present at a concentration of about 80 mg/L to 120 mg/L.

Aspect 74. The reagent solution of aspect 65, wherein the DTNB is present at a concentration of about 100 mg/L.

Aspect 75. The reagent solution of aspect 65, wherein the humectant comprises glycerol, xylitol, sorbitol, glycerol, or propylene glycol.

Aspect 76. The reagent solution of aspect 75, wherein the humectant comprises glycerol.

Aspect 77. The reagent solution of aspect 76, wherein the glycerol is present at a concentration of about 0.1% to 5.0% by volume.

Aspect 78. The reagent solution of aspect 76, wherein the glycerol is present at a concentration of about 0.5% by volume.

Aspect 79. The reagent solution of aspect 75, wherein the humectant comprises xylitol.

Aspect 80. The reagent solution of aspect 79, wherein the xylitol is present at a concentration of about 2% to 10% by weight.

Aspect 81. The reagent solution of aspect 79, wherein the xylitol is present at a concentration of about 4% by weight.

Aspect 82. The reagent solution of aspect 65, further comprising a flavoring or scent.

Aspect 83. The reagent solution of aspect 82, wherein the flavoring or scent is peppermint.

Aspect 84. The reagent solution of aspect 65, further comprising an alcohol.

Aspect 85. The reagent solution of aspect 84, wherein the alcohol is isopropanol or ethanol.

Aspect 86. The reagent solution of aspect 65, further comprising an alkaline earth metal or a transition metal.

Aspect 87. The reagent solution of aspect 86, wherein the metal comprises manganese, magnesium, or cobalt.

Aspect 88. A detection device comprising a solid substrate which comprises a detection region, wherein the detection region is impregnated with the reagent solution of any of aspects 65-87.

Aspect 89. The detection device of aspect 88, wherein the reagent solution has been dried.

Aspect 90. The detection device of aspect 88, wherein the solid substrate is a pad of inert fibers.

Aspect 91. The detection device of aspect 90, wherein the fibers comprise at least one material described in U.S. Pat. No. 7,290,668.

Aspect 92. The detection device of aspect 90, wherein the fibers comprise a TRANSORB® brand material designated R-27378 or R28445 D#4345.

Aspect 93. The detection device of aspect 88, wherein the solid substrate is rectangular, or composed of a die-cut shape or shapes, typically up to about 8 mm×8 mm, and a thickness of about 1.0 mm.

Aspect 94. The detection device of aspect 90-93, wherein the solid substrate further comprises one or more standard regions.

Aspect 95. The detection device of aspect 94, wherein the one or more standard regions comprise a calorimetric standard of a predetermined color and intensity.

Aspect 96. A method of manufacturing a thiol compound detection device comprising: contacting a solid substrate with the reagent solution according to any of aspects 65-87, and drying the device.

Aspect 97. A detection device manufactured by the method of aspect 96.

Aspect 98. A method of detecting halitosis in a subject, comprising contacting a physiological fluid taken from the oral cavity of the subject with the detection device of aspect 88 or aspect 97 to form a physiological-fluid-contacted device, and detecting a thiol compound concentration level in the physiological-fluid-contacted device, wherein a level of at least about 40 micromolar thiol is indicative of halitosis.

Aspect 99. A method of detecting gingivitis in a subject, comprising contacting a physiological fluid taken from the oral cavity of the subject with the detection device of aspect 88 or aspect 97 to form a physiological-fluid-contacted device, and detecting a thiol compound concentration level in the physiological-fluid-contacted device, wherein a level of at least about 80 micromolar thiol is indicative of gingivitis.

Aspect 100. A method of detecting periodontal disease in a subject, comprising contacting a physiological fluid taken from the oral cavity of the subject with the detection device of aspect 88 or aspect 97 to form a physiological-fluid-contacted device, and detecting a thiol compound concentration level in the physiological-fluid-contacted device, wherein a level of at least about 160 micromolar thiol is indicative of periodontitis.

Aspect 101. The method of any of aspects 98, 99 or 100, wherein the detecting is performed by comparing color intensity or absorbance of (a) the physiological-fluid-contacted device to (b) a standard.

Aspect 102. The method of aspect 101, wherein the detecting is performed by eye.

Aspect 103. The method of aspect 101, wherein the detecting is performed by machine.

Aspect 104. The method of aspect 101, wherein the detecting is performed by a spectrophotometer.

Aspect 105. The method of aspect 101, wherein the detecting provides a quantified or semi-quantified signal.

Aspect 106. The method of any of aspects 98, 99 or 100, wherein the physiological fluid is GCF, tongue scrapings, tongue biofilm, gumline biofilm, saliva, or breath.

Aspect 107. A test kit useful for the detection of oral thiol compounds, comprising the reagent solution of aspect 65, the detection device of aspect 88, or the detection device of aspect 97.

Further aspects of the invention. The invention is provided inter alia in the following further aspects.

In normal circumstances many microorganisms live on or in humans without causing harm to these humans. However, an increased number of certain microorganisms can be associated with a disease state. Particularly problematic is an increase in the number of microorganisms that produce significant concentrations of chemicals that are toxic to humans. Such toxins include: volatile sulfur compounds (VSCs), such as hydrogen sulfide, methyl mercaptan, dimethyl disulfide, and dimethyl sulfide. Higher concentrations of volatile sulfur compounds are associated with certain disease states and with socially stigmatized conditions, such as halitosis, or bad breath. It would be desirable to enable facile detection of volatile sulfur compounds in order to facilitate detection of the presence of potentially pathogenic microorganisms and of disease states and conditions with which these microorganisms are associated.

The principal VSCs produced by oral bacteria are hydrogen sulfide and methyl mercaptan. Hydrogen sulfide is produced by the bacterial enzyme L-cysteine desulthydrase, which degrades the amino acid L-cysteine to produce hydrogen sulfide, ammonium and 2-ketopropanate. The other major VSC, methyl mercaptan, is produced by the action of the bacterial enzyme L-methionine gamma lyase, which breaks down the amino acid L-methionine to produce methyl mercaptan, ammonium and 2-ketobutyrate.

Millimolar levels of VSCs have been reported to occur in the gingival crevicular fluid (GCF) of persons with severe periodontal disease. The presence of VSCs imparts a foul odor to the breath of persons with the disease. In addition to being malodorous, VSCs have also been shown to be toxic and adversely affect a number of mammalian enzymes. Production of VSCs by bacteria residing on the dorsum of the tongue and elsewhere within the oral cavity imparts a foul odor to expired breath, resulting in halitosis. The level of VSCs in each of several oral fluids correlates directly with the level of periodontal disease activity. The levels of VSCs in expired air correlate directly with the level of bad breath or halitosis.

While in the art the colorimetric reaction of DTNB may be regarded as optimally performed at pH 8.0, an aqueous solution of DTNB is unstable when stored for several days at room temperature under such conditions. It was unexpectedly found that the inclusion of metal salt and the adjustment of pH around neutrality impart the favorable property of a markedly extended shelf-life. By way of example and not of limitation, it was found that a DTNB mixture was maintained stable for more than one year at room temperature when the mixture included phosphate or imidazole buffer, pH 7.0, and 0.1 mM manganese chloride. Hence the invention provides inter alia a chromogenic composition the absorbance of which correlates directly with the concentration of VSCs in a fluid with which the composition is intermixed and which composition has a shelf-life of at least one year.

An article and/or a method and/or a composition according to the invention is useful for detecting the presence of malodorous toxins found in oral fluid and produced by inter alia bacteria residing on the dorsum of the tongue and in GCF from the gingival sulcus.

For example, in an aspect of a method according to the invention, a sample of oral fluid is obtained by gently contacting at least the matrix portion of an article according to the invention with oral fluid in a subject's oral cavity in such a way that oral fluid from the subject's oral cavity is absorbed into the matrix portion of the article, and then waiting for a period of time of between a few seconds and a few minutes and thereafter observing the color that has developed on the matrix portion of the article, which color is then compared to one or more colors on a color comparator chart that is provided in connection with the article.

By way of example and not of limitation, a method for detection of VSCs according to the invention may have a lower limit of detection on the order of 10 micromolar VSCs and an upper limit of responsive range on the order of 2 millimolar VSCs.

The invention also provides a method for detection of VSCs in expired breath. A subject expires breath onto an article according to the invention held in close proximity to the subject's oral cavity, a condensate of the expired breath contacting and being absorbed into the matrix portion of the article.

The simplicity of use of an article and/or a method and/or a composition according to the invention facilitates in-office testing by health care professionals and home testing by subjects. An article and/or a method and/or a composition according to the invention is more generally useful for the detection of VSCs in samples comprising air, water, oil, and/or another fluid in contact with a foodstuff or a food, and hence is also useful for the detection of products of microbial metabolism, pathogenic microorganisms, halitosis, VSC pollution, or food spoilage or contamination.

The invention is provided in numerous embodiments and can be discerned, inter alia, in various examples. The following examples provide an illustrative but non-limiting description of the breadth and applicability of the invention.

Example 1

Manufacture of an Embodiment of an Article According to the Invention

An absorbent material is selected. A sheet of the selected absorbent material is soaked in a solution that contains a solvent and a detection reagent and optionally additional components. After a period of time, the sheet is removed from the solution and dried. The dried sheet is affixed to a plastic backing to form a sheet-backing laminate. The sheet-backing laminate is cut into strips, each of which strips is an article according to the invention.

Example 2

Absorbent Material

A material such as is described in U.S. Pat. No. 7,290,668 or another similar material may be used as an absorbent material. A material such as a TRANSORB® brand material designated R-27378 or R28445 D#4345 and available from Filtrona Fibertec, Richmond, Va., US, may be used as an absorbent material.

Example 3

Detection Reagent

A detection reagent may comprise 5,5'-dithiobis-(2-nitrobenzoic acid); 5-(2-aminoethyl)-dithio-2-nitrobenzoic acid; N,N'-bis(4-nitrobenzylidene)-4,4'-dithiodianiline; N,N'-bis(3-nitrobenzylidene)-4,4'-dithiodianiline; N,N'-bis(2-nitrobenzylidene)-4,4'-dithiodianiline; N,N'-bis(2,4-dinitrobenzylidene)-4,4'-dithiodianiline; and/or N,N'-bis(4-nitrocinnamalylidene)-4,4'-dithiodianiline. A ditiodianil compound such as is described in any of examples 1-13 of U.S. Pat. No. 4,414,414 may be suitable as a detection reagent.

Example 4

Solution that Contains Solvent and Detection Reagent

Water may be used as solvent for 5,5'-dithiobis-(2-nitrobenzoic acid). A nonaqueous solvent may be used as solvent for N,N'-bis(4-nitrobenzylidene)-4,4'-dithiodianiline; N,N'-bis(3-nitrobenzylidene)-4,4'-dithiodianiline; N,N'-bis(2-nitrobenzylidene)-4,4'-dithiodianiline; N,N'-bis(2,4-dinitrobenzylidene)-4,4'-dithiodianiline; and/or N,N'-bis(4-nitrocinnamalylidene)-4,4'-dithiodianiline.

Example 5

Optional Additional Components of Solution that Contains Solvent and Detection Reagent For an aqueous solution, a water-miscible alcohol known in the art, such as isopropanol, may be included to facilitate drying of the sheet. A buffer known in the art, such as sodium phosphate, may be included for stabilization of pH at close to neutrality and hence of the detection reagent. A humectant known in the art, such as xylitol, sorbitol, glycerol, or propylene glycol, may be included so that an article according to the invention may remain slightly moist and not needlessly brittle. A cosmetically acceptable salt of a divalent cation known in the art, such as manganese chloride, magnesium chloride, or cobalt chloride, may be included for color-fastness of an unused article according to the invention. A cosmetically acceptable chelator of divalent cations known in the art, such as ethylenediaminetetraacetic acid (EDTA), may be included for stabilization of color developed during use of an article according to the invention. A flavorant known in the art, a colorant known in the art, and/or an antimicrobial known in the art may optionally be included as well.

Example 6

Direct and Indirect Contact Devices

In a first exemplary embodiment, an article according to the invention is in the shape of a thin and shallow right rectangular prism. Occupying the terminal portion of one of the prism's two faces of largest surface area, and affixed thereto, is a right rectangular prismatic first pad. The first pad contains a detection reagent. This embodiment is intended for direct contact of a sample with the detection reagent. In a second exemplary embodiment, for indirect contact of a sample with the detection reagent, a right rectangular prismatic second pad is placed at the opposite terminus of the same face to which the first pad is affixed as in the first exemplary embodiment, and the article is crimped along the latitudinal axis of this face so as to have a "V" shape, with the first pad at the terminus of one arm of the "V" and the second pad at the terminus of the other arm. In this embodiment, the second pad lacks detection reagent. The second pad is contacted with a sample. The second pad is then contacted with the first pad, thereby transferring at least a portion of the sample from the second pad to the first pad.

Example 7

Choice of combination of Pad Color and Detection Reagent for Ease of Visualization of Result Under appropriate conditions, DTNB provides a yellow-colored signal upon reaction with thiol compounds. In an embodiment, an article similar to the first exemplary embodiment above is made with a white pad. It is observed that faint yellow colors are sometimes difficult for the human eye to discern with respect to a comparator against which the DTNB-provided yellow-colored signal is to be compared which bears a swatch of white and swatches of various shades of yellow corresponding to various thiol concentrations. In an alternative embodiment, an article similar to the first exemplary embodiment above is made with a blue pad. It is observed that yellow colors developed on this blue background can appear green to the human eye and can in some instances be easier to discern than yellow colors developed on a white background. For this alternative embodiment, a comparator is provided against which the DTNB-provided signal is to be compared which bears a swatch of blue (to match the unreacted pad) and swatches of various shades of green corresponding to various thiol concentrations.

Example 8

Use of an article According to the Invention for Diagnostic Purposes: Clinical Study of a Salivary Test Strip to Screen for Periodontal Disease A saliva test strip according to the invention with a porous pad impregnated with a chromogenic reagent that detects microbial sulfur compounds was prepared for and used in this study. This study compared the saliva strip (SS) scores in subjects with and without periodontal diseases and examined the relationship between SS scores and clinical measures of periodontal status. Seventy-three subjects were enrolled, mean age (SD) 44.73 (19.61), age range 23 to 85, percent males 55%, percent Caucasians 44%. Periodontal evaluations including plaque index (PI), gingival index (GI), clinical periodontal attachment levels (AL) and bleeding on probing (BOP) were performed on 6 sites per tooth. Subjects were divided into 3 groups: periodontally healthy (no loss of attachment and no gingival bleeding, 18 subjects), gingivitis (no loss of attachment and presence of gingival bleeding, 32 subjects) and periodontitis (loss of attachment>5 mm in 5 or more teeth, 23 subjects). Chromogenic strips were used to collect salivary fluid from the gingival margin of all present teeth (1 strip per quadrant). Color reaction was scored based on a color chart. The scoring examiner was blinded to clinical status. Good to moderate correlations were found between average SS scores and GI (r=0.6, p=0.001) and AL (r=0.47, p=0.001). Analysis of variance showed significant differences in SS scores among the three study groups (p=0.03); post-hoc analysis showed difference between health and periodontitis (p=0.01). The results suggested these strips were useful as a screening test for periodontal diseases. They were simple to use, provided a rapid result, and did not require clinical expertise. The same test could be performed easily in any medical/dental setting.

Example 9

Apparatus and Method for Detecting/Estimating Dissolved Oral Thiols

Oral halitosis and periodontal diseases very often involve the microbial production of Volatile Sulfur Compounds (VSCs), primarily hydrogen sulfide and methyl mercaptan. Historically, efforts have focused on detecting their presence in exhaled breath, rather than within microbial biofilms. The objective of this study was to develop test strips targeting dissolved thiols, which provide rapid, visual results, are easy to use, and are non-irritating to oral tissues. Various materials were screened for their ability to provide visually discernable responses to dissolved thiols, after pretreatment with a solution containing a thiol detection reagent according to Aspect 7 of the present invention. The propensity of the dried detection reagent to leach from the pad was estimated spectrophotometrically, by challenging rinse-fluid with added thiol. Prototype test strips were placed into a stability study in order to estimate shelf life. Irritancy testing was performed by an independent lab. Finally, the concentration of detection reagent was varied, to determine if different "cut-off" result colorations could be achieved. A porous pad material was identified, which had good physical characteristics and was compatible with the thiol detection reagent and its chromogenic product. Once dried onto the pad, the reagent showed a low propensity to leach upon rehydration, maintained good spectral responses, and showed reasonable stability over time. The reagent was found to be non-irritating to cultured gingival tissue cells, when compared to standard oral care products. Finally, by raising or lowering the reagent concentration (amount of detector in the pad), we found we could manipulate the plateau coloration of the test. These results suggested test strips embodying the present invention might be useful as aids in detecting causative agents of halitosis and periodontal diseases.

Example 10

Detection of Dissolved Oral Thiols Using Prototype Test Strips

Gram-negative anaerobes are generally responsible for sulfur compounds characteristic of halitosis and periodontal disease. When active, they can be detected by signature metabolic activities, for instance, the production of hydrogen sulfide and methyl mercaptan. These can be detected in the gas phase, e.g., in breath exhaled through the mouth, though such techniques can require costly instrumentation. Accordingly, prototype test strips were prepared that were relatively inexpensive, easy to use and interpret, and which could detect volatile and non-volatile thiols dissolved aqueous fluids. The objectives of this study were: 1) determine the test strips' ability to detect thiol in oral fluids on the dorsum of the tongue; 2) to determine the test strips' ability to detect thiols in oral fluids on the gingival surface; 3) to compare the findings from the tongue surface to that of the gingival surface; and 4) to compare the test strip outcomes to samples analyzed using gas chromatography. Prototypes were prepared, which resemble and report like disposable pH test strips. They consisted of a porous pad on a flexible plastic backing. Prior to assembly, the pad was treated with a thiol detector solution, and dried. Using standard thiol solutions, color charts were created, whose color chips (swatches) related to specific concentration of thiols. The charts in turn were used to estimate thiol concentration in unknown fluid samples. Dissolved thiols were detected in fluid collected from the dorsum of the tongue, as well as from fluid on gingival surfaces. In a small study population, the average levels of dissolved thiols from the tongue dorsum (15 µM) were relatively lower than those found on the gingival surface (88 µM). Overall, individuals with detectable oral fluid thiols (either source) showed generally higher levels of volatile thiols, as measured by gas chromatography. Accordingly, a quick and easy assay was developed, which was able to detect thiols dissolved in oral fluids. Tongue dorsum and gingival biofilms had potential diagnostic value, and each appeared related to the primary volatile thiols measurable in exhaled breath. These results suggested that test strips like these could also be used generally, where an estimate of dissolved thiols is desired.

Additional, further descriptions and examples illustrative of the invention are provided below.

The invention provides inter alia reagent solutions, detection devices, and chromogenic methods of detecting thiol compounds, including volatile sulfur compounds (VSCs) produced by oral bacteria residing on the dorsum of the tongue and in the gingival sulcus. As used herein, a "thiol compound" refers to a molecule having a thiol or "—SH" functional group or to a molecule having a thiolate or sulfide anion. Examples of sulfur-containing molecules include hydrogen sulfide and methyl mercaptan (methanethiol). In certain embodiments of the invention, the absorbance of a chromogenic composition according to the invention correlates directly with the concentration of thiol compound in a fluid with which the composition is intermixed.

Compositions and methods according to the invention are useful for detecting the presence of malodorous toxins produced by bacteria residing on the dorsum of the tongue and in GCF obtained from the gingival sulcus.

For example, in an aspect of a method according to the invention, tongue scrapings are obtained by gently rubbing a test strip against the dorsum of the tongue to form a scraping-laden applicator tip. Additionally, or alternatively, the test strip can be moistened with saliva. In another embodiment, a GCF sample is obtained by inserting a sterile paper absorbent point into the gingival sulcus. The color of the chromogen-developed test strip or absorbent point is compared to standards on a color-coded chart or to an internal control. In certain embodiments, the chart is scaled in shades of yellow, from LOW (light yellow) corresponding to 20-100 micromolar thiol, MEDIUM (yellow) corresponding to 100-200 micromolar thiol, to HIGH (bright yellow) corresponding to >200 micromolar thiol.

The present invention provides, inter alia, a reagent solution containing a buffer, 5,5'-Dithiobis(2-nitrobenzoic acid) (DTNB), and a humectant. When used in connection with the invention, "DTNB" refers to 5,5'-Dithiobis(2-nitrobenzoic acid). DTNB is also known as Ellman's reagent and has CAS number 69-78-3. Without intending to be bound by theory, the inventors believe that it is known in the art that DTNB reacts with the sulfide or thiolate anion formed from the —SH functional group present in $H_2S$ or $CH_3SH$. In such reaction, one of the disulfide sulfurs of DTNB is attacked by the $HS^-$ or $CH_3S^-$ anion, whereupon the 5-thio-2-nitrobenzoate anion (TNB) is released. TNB exists in equilibrium with the tautomeric thioquinone. The thioquinone has an absorption (absorbance) maximum at 412 nm with a molar extinction coefficient of 13,600 $M^{-1}$ $cm^-$. This allows for the reaction to be quantified spectrophotometrically or visually by the increase in the yellow color of the mixture.

The present invention also provides a detection device that is a solid substrate, such as a porous solid substrate, that includes a detection region, wherein the detection region is impregnated with a reagent solution containing a buffer, 5,5'-Dithiobis(2-nitrobenzoic acid) (DTNB), and a humectant.

The present invention also provides a method of manufacturing a detection device useful for the detection of thiol compounds in physiological fluids. The manufacturing method includes contacting a solid substrate with the reagent solution containing a buffer, 5,5'-Dithiobis(2-nitrobenzoic acid) (DTNB), and a humectant, and drying the device.

The present invention also provides a detection device useful for the detection of thiol compounds in physiological fluids manufactured by the method described above.

The present invention provides a method of detecting halitosis in a subject by contacting a physiological fluid taken from the oral cavity of the subject with the detection device described above to form a physiological-fluid-contacted device, and detecting a thiol compound concentration level in the physiological-fluid-contacted device, wherein a level greater than about 40 micromolar thiol is indicative of halitosis. In certain embodiments, the thiol compound concentration level is between about 40-200 micromolar.

The present invention provides a method of detecting gingivitis in a subject by contacting a physiological fluid taken from the oral cavity of the subject with the detection device described above to form a physiological-fluid-contacted device, and detecting a thiol compound concentration level in the physiological-fluid-contacted device, wherein a level greater than about 80 micromolar thiol is indicative of gingivitis. In certain embodiments, the thiol compound concentration level is between about 80-400 micromolar.

The present invention provides a method of detecting periodontitis in a subject by contacting a physiological fluid taken from the oral cavity of the subject with the detection device described above to form a physiological-fluid-contacted device, and detecting a thiol compound concentration level in the physiological-fluid-contacted device, wherein a level greater than about 160 micromolar thiol is indicative of periodontitis. In certain embodiments, the thiol compound concentration level is between about 160-600 micromolar.

The present invention further provides a test kit useful for the detection of thiol compounds in physiological fluids from the oral cavity, a test kit that includes the reagent solution containing a buffer, 5,5'-Dithiobis(2-nitrobenzoic acid) (DTNB), and a humectant, the detection device that is a solid substrate that includes a detection region, wherein the detection region is impregnated with the reagent solution containing a buffer, 5,5'-Dithiobis(2-nitrobenzoic acid) (DTNB), and a humectant, or the detection device made by the method described above.

Reagent Solutions.

The inventors have developed a reagent solution that is useful in detecting halitosis, gingivitis and/or periodontal disease. The reagent solution contains a buffer, a detection agent, and a humectant. The buffer is used to keep the solution at a pH that is close to physiological pH, which is a pH of about 7.0. The pH of the present reagent solution can be in the range of about 6.5 to 8.5, or in the range of about 6.5 to 7.5. In certain embodiments, the pH of the reagent solution is at 7.0. In certain embodiments, the buffer is a sodium phosphate buffer at a concentration of about 5 mM to 200 mM. In certain embodiments, the buffer is a sodium phosphate buffer at a concentration of about 20 mM to 150 mM. In certain embodiments, the buffer is a sodium phosphate buffer at a concentration of about 100 mM.

The reagent solution of the present invention contains a detection agent. In certain embodiments, the detection agent is 5,5'-Dithiobis(2-nitrobenzoic acid) (DTNB). In certain embodiments the DTNB is present at a concentration of about 10 mg/L to 150 mg/L. In certain embodiments the DTNB is present at a concentration of about 30 mg/L to 150 mg/L. In certain embodiments the DTNB is present at a concentration of about 80 mg/L to 120 mg/L. In certain embodiments the DTNB is present at a concentration of about 100 mg/L.

The reagent solution of the present invention contains a humectant. The humectants of the present invention are of a food or pharmaceutical grade. Suitable humectants include glycerol, xylitol, sorbitol, glycerol, or propylene glycol. In certain embodiments, the reagent solution includes glycerol that is present at a concentration of about 0.1% to 5.0% by volume. In certain embodiments, the glycerol is present at a concentration of about 0.5% by volume. In certain embodiments, the reagent solution includes xylitol. In certain embodiments, the xylitol is present at a concentration of about 2% to 10% by weight. In certain embodiments, the xylitol is present at a concentration of about 4% by weight.

The inventors found that for certain applications, glycerol and xylitol worked well to maintain the starting color of the pad material (off-white), in order to provide the best 'stage' for detecting the color changes associated with thiol/DTNB reactions. In addition, xylitol imparts a sweet flavor (and is used in many oral care formulations), and glycerol imparts a softer feel to the pad surface. Adding glycerol, a humectant and an emollient, helped to maintain the initial pad color upon drying, and also provided a smoother feel to the pad.

The reagent solution of the present invention may also contain a flavoring or scent, such as peppermint. In one embodiment 0.5 g hydroxypropyl beta-cyclodextrin was used as the carrier, to which was added 0.16 mL peppermint oil. This mixture, in 10 mL of water, was used as an additive to 100 mL of reagent solution. Thus, per 1 L standard reagent solution amount, the flavor/scent additives are 5 g hydroxypropyl cyclodextrin and 1.6 mL peppermint oil, with mixing of the complexed oil into 100 mL water, before adding it to the bulk of the reagent solution.

The reagent solution of the present invention may also contain an alcohol, such as isopropanol. In certain embodiments, 70% isopropanol was used. The alcohol was a USP grade. In certain embodiments, up to one-tenth volume of reagent was alcohol. The presence of the alcohol allows the detection reagent to dry more quickly onto a solid substrate such as a pad material.

The reagent solution of the present invention optionally may also contain an alkaline earth metal or a transition metal. Examples of suitable metals include manganese, magnesium, and, especially with respect to an indirect contact device, cobalt. At room temperature and atmospheric pressure, hydrogen sulfide tends to escape from an aqueous liquid in which that hydrogen sulfide has been dissolved, when that aqueous liquid is contained in an open vessel, and into air above the open vessel. The devices and methods of the present invention were surprisingly successful in measuring levels of thiol compounds in liquid samples as well as in gaseous samples.

Detection Devices.

The inventors have developed detection devices that are useful in detecting halitosis, gingivitis and/or periodontitis. In certain embodiments, the detection device is a solid substrate, which contains a detection region, wherein the detection region is impregnated with the reagent solution described above. In certain embodiments, the reagent solution has been dried onto the solid substrate. The inventors have found that once the reagent solution was dried onto the solid substrate, it was quite stable. In certain embodiments, a metal ion (such as manganese) can be added.

In certain embodiments, the solid substrate is a porous pad of inert fibers. In certain embodiments, the fibers are composed of at least one material described in U.S. Pat. No. 7,290,668. In certain embodiments, the fibers are composed of a TRANSORB® brand material designated R-27378 or R28445 D#4345. In certain embodiments, a colored (e.g., blue) pad may be used instead of a white pad. The blue coloration allows for alternative color development possibilities; being able to change the starting color of the pad also allows one to effectively manipulate threshold concentrations corresponding to different stages of the disease process. In certain embodiments, a "standard" pad or colored tape (i.e., of a static color) is placed immediately adjacent to the "detector" pad. In other embodiments, these "standard" and "detector" regions are separated from one another by a small gap, showing a white background between them. When comparing certain color combinations visually, a slight gap between the two regions allows for better visibility. It was found that this was true when the detection depends upon a yellow indicator, and when the differences in color intensities and/or shades are subtle, rather than overtly obvious. In certain embodiments, an internal control can also be used.

In certain embodiments, the solid substrate may be cut or otherwise formed to certain desired shapes and/or sizes (e.g., by die-cutting). In certain embodiments, the solid substrate such as a pad may be between about 0.8 mm and about 1.2 mm thick, between about 5.5 mm and about 8 mm wide, and between about 7 mm and 8 mm long. Shapes other than right rectangular prismatic shapes may be formed, for example within a field of roughly 8 mm×8 mm, such as to form the circles, diamonds, and plus-signs. Other desired shapes may be die-cut as well. Also, gaps between reactive and non-reactive portions can be incorporated as well.

In certain embodiments, in addition to having a detection region, the detection device also has a standard region. Thus, the user of the detection device is able to readily compare the detection region to the standard region to determine whether the test was positive or negative. In certain embodiments, the standard region is a calorimetric standard of a predetermined intensity.

In one embodiment, a test stick is used in a direct contact application (FIG. 1). In this embodiment, a test stick is used that contains a pad at one end of the stick, wherein the pad is impregnated with the test solution. The test solution in certain embodiments has been dried, allowing the solvent to evaporate. The pad is placed in direct contact with the sample (e.g., saliva). After a period of time, the pad is examined to determine the development of color.

Certain embodiments include direct contact test devices (FIGS. 2A-2D). Upon contact with a test sample the reactive pad may or may not change color (depending on the level of thiols present in the sample). A comparator's color does not change during the test, since there is no detection reagent present in the comparator pad. The comparator may have a) the same color as the starting color of the reactive pad (e.g., FIG. 2A, wherein higher thiol levels in a sample cause the reactive pad to diverge progressively from the comparator color), or b) a target 'cut-off' color (e.g., FIG. 2B, wherein progressively higher thiol levels cause the reactive pad to converge upon, or perhaps surpass the comparator color, at a set time point). More than one comparator may be employed, such as when, for example, both initial and cut-off comparator colors are present, immediately above and below the reactive pad, respectively (FIG. 2C). Accordingly, the cut-off color may indicate the color a reactive pad might attain, if a certain thiol level was present in the sample. The nested reactive pad may (depending on the thiol concentration) attain or surpass the color of the comparator. Gaps surrounding the reactive pads (see earlier discussion, above), may facilitate better discernment of color changes. FIG. 2D depicts a situation in which the pads of FIG. 2B are reversed in position.

FIG. 3 (also direct contact format) depicts alternative test strip configurations, in which a die-cut (shaped) reactive pad is nested within the comparator. For purposes of illustration, shapes presented here are circles, diamonds, or crosses. FIGS. 3A-C depict a circular reactive pad nested within the comparator. The nested reactive pad may (depending on the thiol concentration) attain or surpass the color of the comparator. Matching or surpassing the comparator color as an indication of a positive test is shown by FIGS. 3A and 3B. Surpassing alone as an indication of a positive test is shown by FIGS. 3C-E. FIGS. 3C and 3D are analogous to 3C, but have non-circular reactive pads. Not shown in this series are gaps surrounding the reactive pads (see earlier discussion, above), which may facilitate better discernment of color changes.

The invention provides inter alia indirect contact devices (e.g., FIGS. 4A and 4B). In one embodiment of the present invention (FIG. 4A), the reagent is applied at the distal end of a cylindrical porous matrix, the reagent migrates slightly into the part, towards the proximal end. The material is then dried, and placed in a clear protective housing. During use, the sample is applied to the proximal end, and the fluid migrates towards the distal end, and fills the material. When the sample comes into contact with the detection reagent at the distal end, it can react with the reagent, causing a color change. In another embodiment of the present invention (FIG. 4B), the reagent solution is applied to one of two cylinders, and allowed to dry. The cylinder impregnated with the reagent is placed into a clear protective housing. A second cylinder (for the sample) is placed near, but not in direct contact with, the first cylinder. During use, sample is applied to and fills the 'sample' cylinder. Then the sample cylinder is brought into contact with the reagent cylinder, and sample fluid migrates from the sample cylinder into the detection cylinder. Thiols in the sample reacting with the detection reagent will then be visualized in the detection cylinder.

In another embodiment of an indirect contact device (e.g., FIG. 5), sample contacts a flat surface, which then conducts it to the reactive pad. A color change (or lack thereof) in the reactive pad is then viewed through a clear window on the face of the test device opposite the sample application face.

Figure 6:
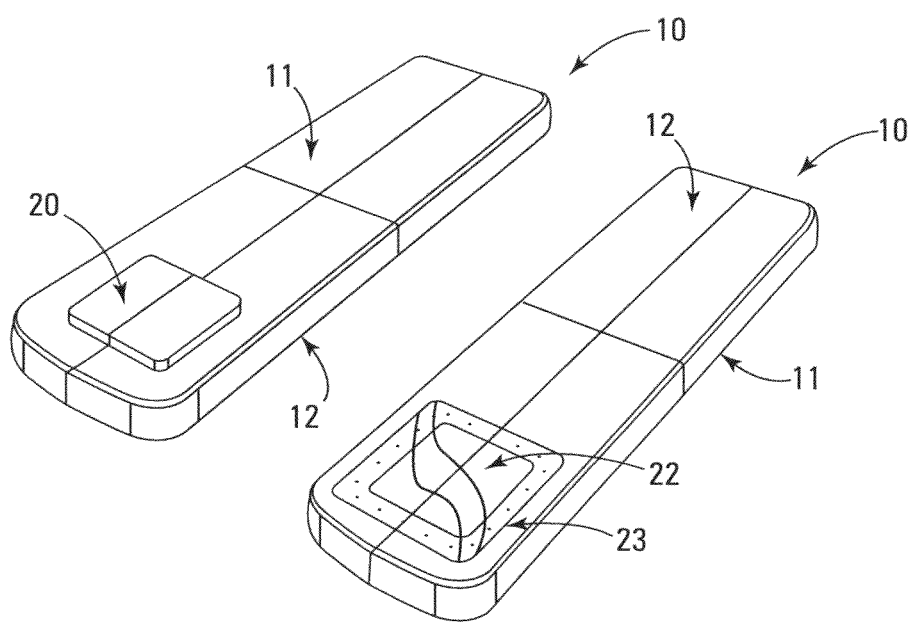
FIG. 6 depicts an example of an indirect contact device (Masked type).

One embodiment of a detection device of the present invention is shown in FIG. 6. The detection device 10 has a sample side 11 and a result side 12. Positioned on side 11 is the sample pad 20. Once sample fluid enters sample pad 20 on side 11, it is transmitted to the reaction pad 22, which faces side 12. A clear cover 23 covers the result pad 22.

Other embodiments of indirect contact devices are shown in FIGS. 7A-7D. FIGS. 7A and 7B are examples of "foldover" devices. In FIG. 7A a device 30 is shown, which has a support 31, a sample collection pad 32 and a reagent pad 33. A reagent solution is impregnated into the reagent pad 33, and may optionally be dried therein. A sample (e.g., saliva) is applied to the sample collection pad 32, and the support is folded such that the sample collection pad 32 and the reagent pad 33 are brought into contact with each other. When folded over, the sample collection pad 32 and the reagent pad 33 may be gently squeezed such that the fluid from the sample collection pad 32 moistens and transfers to the reagent pad 33. The user then unfolds the device and views the result (e.g., color change vs. no color change), seen within the reagent pad.

FIG. 7B shows a test device 40 having a sample collection region 41, a reagent region 42, and a reaction window 45. A reagent solution is impregnated into the reagent region 42, and may optionally be dried therein. A sample (e.g., saliva) is applied to the sample collection region 41, and the support is folded such that the sample collection region 41 and the reagent region 42 are brought into contact with each other. When folded over, the sample collection region 41 and the reagent region 42 may be gently squeezed such that the fluid from the sample collection region 41 moistens the reagent region 42. Instead of unfolding the device to view the result (as in FIG. 7A), the user simply turns the test device over, to view the result through a clear (e.g., plastic) window 45.

FIGS. 7C and 7D show detection devices employing a "slider" concept. In the embodiment shown in FIG. 7C, the device 50 is composed of a strip 51 that includes a sample collection region 52 and a clear (e.g., plastic) sleeve 53. The sleeve 53 includes a reagent region 54, attached within it. A reagent solution, which may be dried, is impregnated into the reagent region 54. The user removes the strip 51 from the sleeve 53, and applies sample to sample collection region 52. The user then slides strip 51 into sleeve 53, so that the sample collection region 52 contacts reagent region 54. The user may gently squeeze the sample collection region 52 and reagent region 54 such that the fluid from the sample collection region 52 moistens the reagent region 54. In one embodiment, the reagent region 54 is an integral part of the sleeve 53.

FIG. 7D shows a detection device 60 that includes a sample collection region 62, a sleeve 63, and a reaction window 65. The sleeve 63 includes a reagent region 64. A reagent solution, which may be dried, is impregnated into the reagent region 64. The user applies sample to sample collection region 62, then slides the sleeve so that reagent region 64 contacts the sample collection region 62. The contact is tight enough to allow sample to migrate into the reaction region 64. The user then reads a result through a clear (e.g., plastic) window 65, which is positioned immediately above the reaction region 64.

Figure 8A:
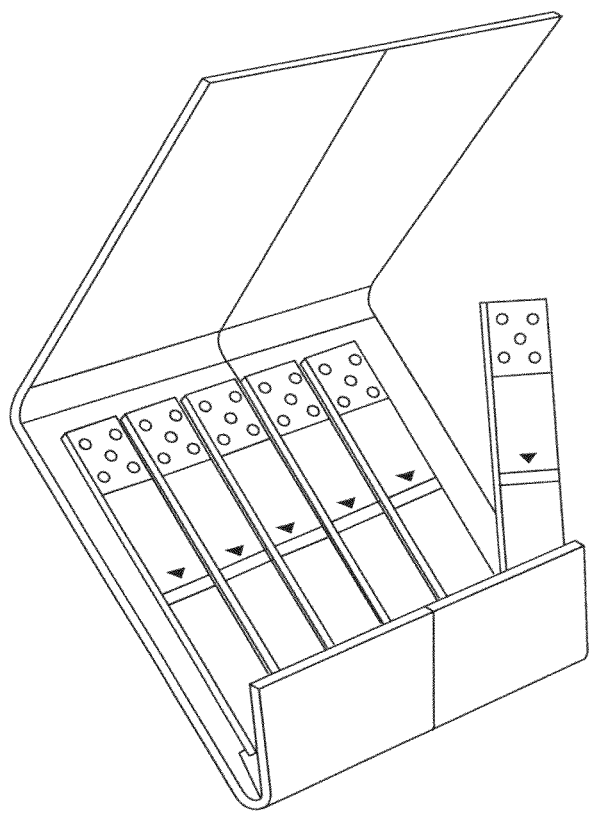
Figure 8C:
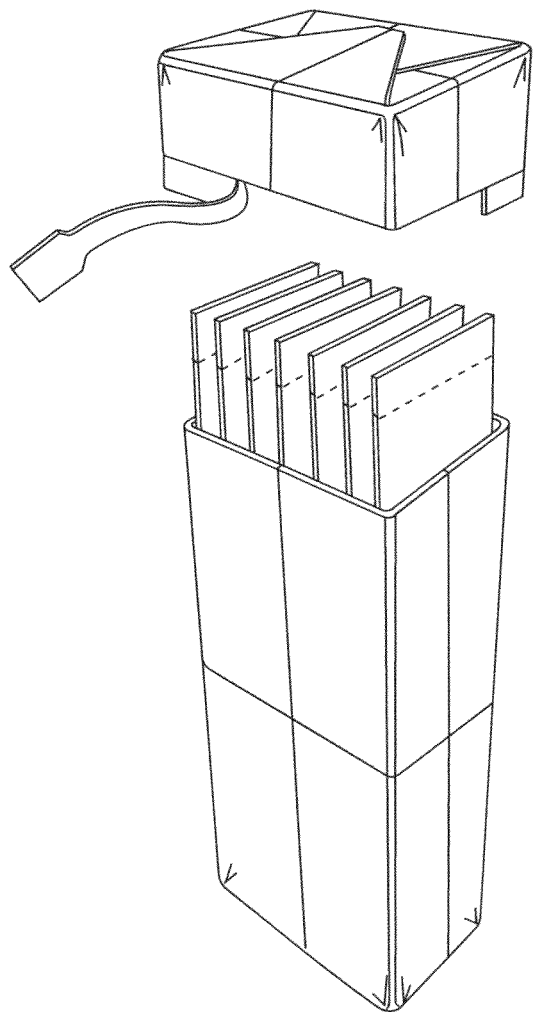
Figure 8D:
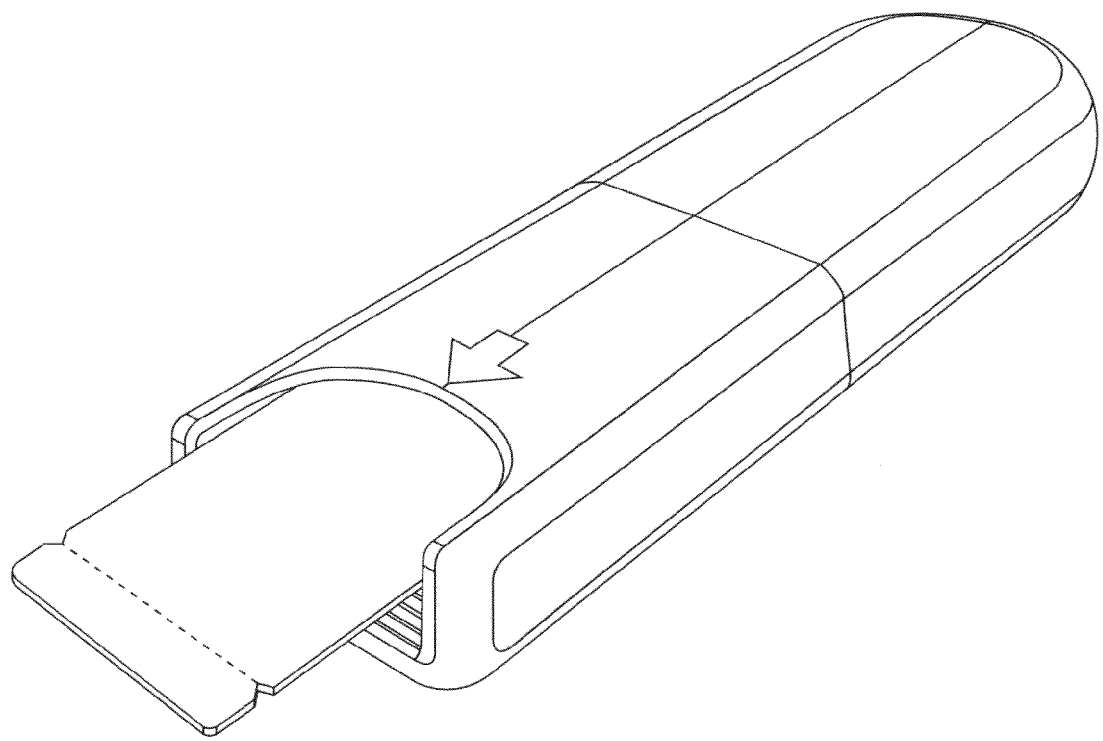
Figure 8E:
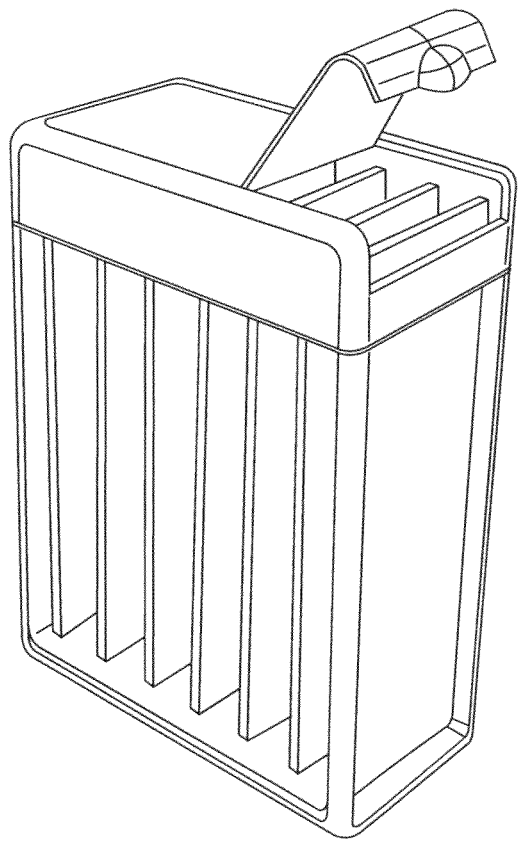
Figure 8F:
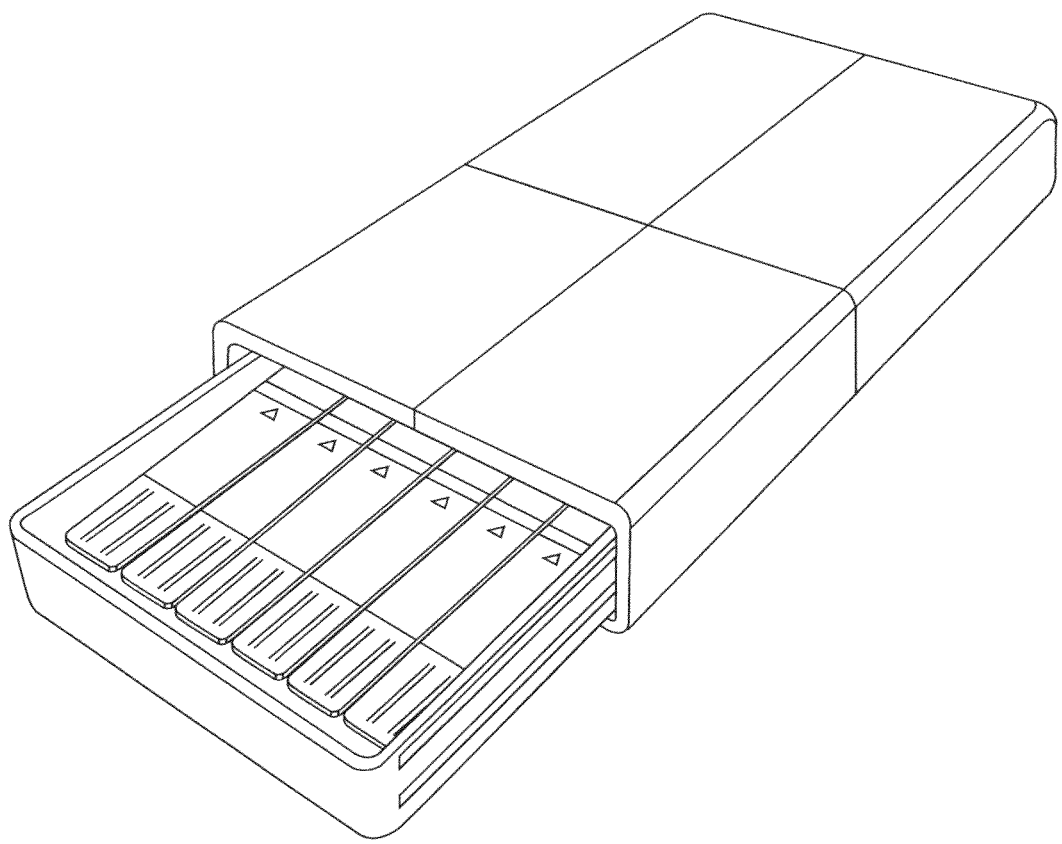

FIGS. 8A-8F depict various alternative packaging designs for the present invention. FIG. 8A depicts a "matchbook" design. Individual strips are removed by the user. Each strip may optionally be wrapped, such as with foil. Each book holds a convenient number of test strips, such as 6-12 per book. FIG. 8B depicts a foil wrap and box design. The test strips are stored in bulk in a box, such as a cardboard or plastic box, and are packaged in foil rows. Each foil row contains a convenient number of test strips, such as 5-10 per row. FIG. 8C depicts a "pack of gum" design. The test strips are stored in bulk in a box, such as a cardboard or plastic box, and are individually packaged in foil wrappers. FIG. 8D is a similar design to FIG. 8C, only the packaging is a plastic housing. Each test strip is individually wrapped. In one embodiment, 5-10 test strips are packaged in the dispenser. FIG. 8E provides a dispenser with a lid. FIG. 8F provides a sliding-drawer type dispenser.

Figure 9:
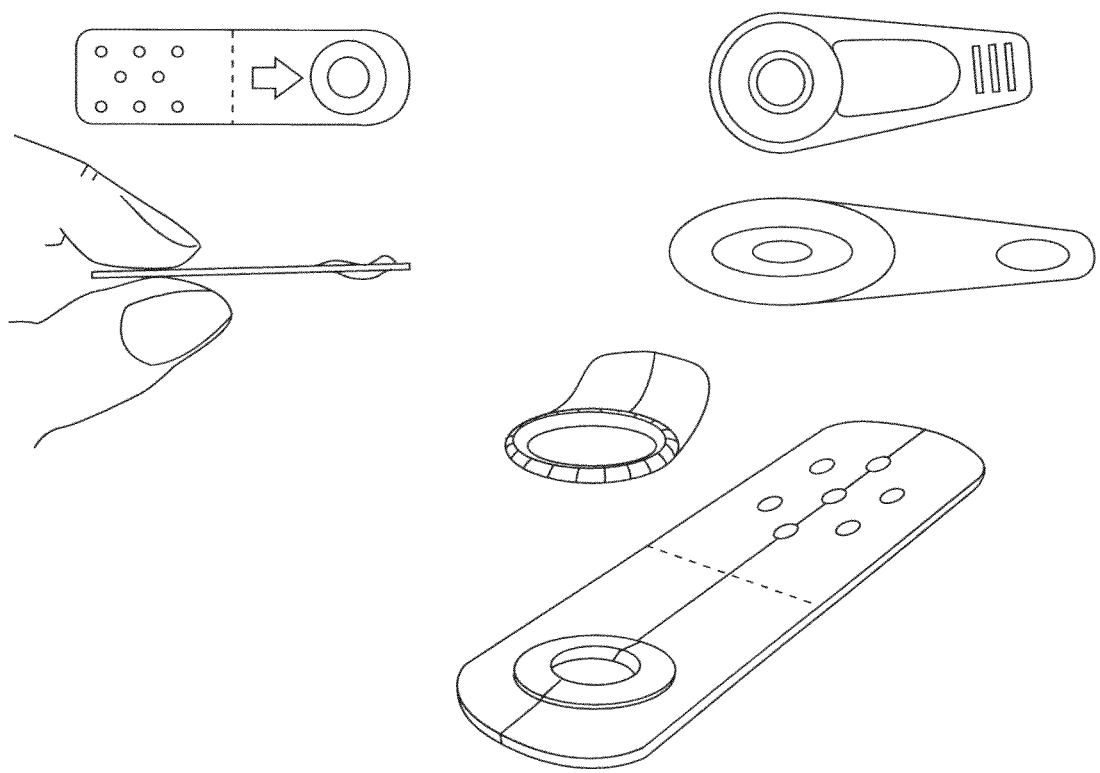
FIG. 9 depicts an example of an indirect contact device.

The present invention further provides a molded test housing (FIG. 9). In one embodiment the reaction region is encased in a molded plastic part. In this embodiment, the reagent region has been impregnated with a detection reagent solution, which has been dried onto the reaction region. The reaction region is covered by a removable porous membrane or pad, which serves as the sample region. Sample (e.g., saliva) is collected on the sample pad, and then migrates to the reagent region adjacent to it. Instead of viewing the result through a clear window (as one would using the device shown in FIG. 6), the sample pad is removed and discarded, revealing the reagent region. The result is viewed and interpreted.

Figure 10:
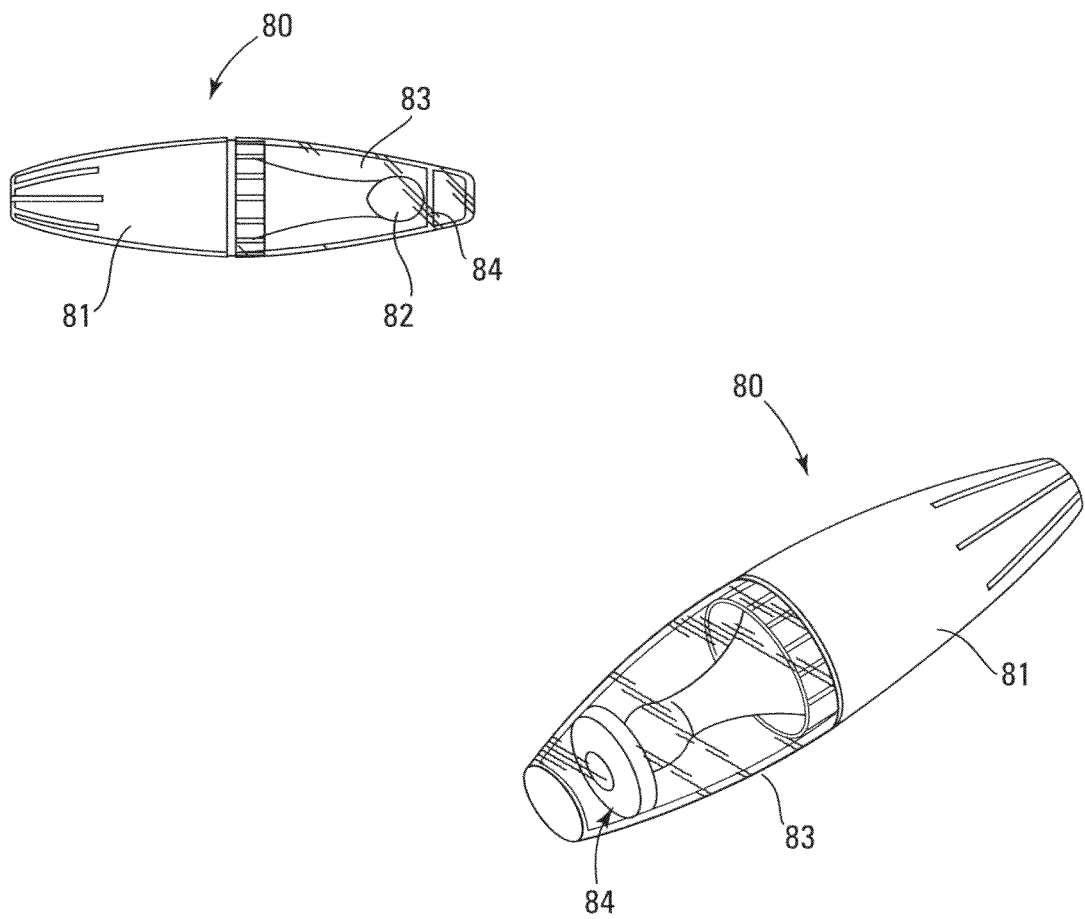
FIG. 10 depicts an example of an indirect capped collector device.

The present invention further provides a capped collector device (FIG. 10). FIG. 10 shows a capped detection device 80. In one embodiment, the detection device includes a handle 81, a sample collection region 82, a cap 83, and a reagent region 84. A reagent solution, which may be dried, is impregnated into the reagent region 84. In an alternative embodiment, the detection device 80 includes a handle 81, a sample collection region 82, and a cap 83. A reagent solution, which may be dried, is impregnated into the sample collection region 82. In this embodiment, a protective cap is removed from the test device, and a sample collection pad/swab is inserted into the subject's mouth. The sample collection pad/swab is contacted with the test sample. The sample collection pad/swab is then removed from the mouth, and the device is re-capped. In some embodiments, the sample collection pad/swab has been impregnated with a detection reagent, which may optionally be dried onto the sample collection pad/swab. In other embodiments, a reagent pad that has been impregnated with a detection reagent, which may optionally be dried onto the reagent pad, is integrated into the protective cap. In this embodiment, when the device is re-capped, this action brings the sample collection pad/swab into contact with the reagent pad. In either embodiment, after an appropriate period of time, the reagent pad is observed to determine the degree of color change.

Method of Manufacture and Manufactured Device.

The present invention includes a method of manufacturing a detection device for measuring the amount of thiol compounds in sample containing a physiological fluid. The manufacturing method includes contacting a solid substrate with a reagent solution as described above, and drying the device.

The present invention further includes a detection device for measuring the amount of thiol compounds in sample containing a physiological fluid manufactured by the method described above.

Method of Detection of Thiol Compounds in Physiological Samples.

The present invention provides a method of detecting halitosis, gingivitis and/or periodontitis in a subject. The method involves contacting a physiological fluid taken from the oral cavity of the subject with one of the detection devices described above to form a physiological-fluid-contacted device, and detecting the concentration level of thiol compounds in the physiological-fluid-contacted device. A level of at least about 40 micromolar is indicative of halitosis, a level of at least about 80 micromolar is indicative of gingivitis, and a level of at least about 160 micromolar is indicative of periodontitis. In certain embodiments, the detection device is capable of detecting the presence of thiol compounds as low as the 10-20 micromolar level.

In certain embodiments, the physiological fluid is removed from the oral cavity of the subject and then placed in contact with the detection device. In other embodiments, the detection device is inserted into the oral cavity of the subject such that the physiological fluid directly contacts the device in situ. For example, a test strip is inserted into the mouth, and the reactive matrix directly contacts the saliva of the subject. Surprisingly it was discovered that a prototype reagent solution containing the detection reagent was not irritating to the mouth, even when oral tissues were contacted directly with a DTNB-containing swab.

In certain embodiments, the detection device is used in a "direct contact" method. In this method, the device with detector-impregnated matrix makes direct contact with user. For example, the detection region of the device is a simple pad on end of strip. In certain embodiments, the detection device is used in an "indirect contact" method. In this method, the detector-impregnated matrix makes no direct contact with user. The contact is made over time, by diffusion of a fluid sample, or physical movement of a collected sample matrix so that the fluid sample or the collected sample matrix contacts the detector-impregnated matrix.

In certain embodiments, the detecting is performed by comparing color intensity or absorbance of (a) the physiological-fluid-contacted device to (b) a standard. In certain embodiments, the detecting is performed by eye. In other embodiments, the detecting is performed by machine, such as by a spectrophotometer (e.g., reflectance spectrophotometer). In certain embodiments, the detection step provides a quantified or semi-quantified signal, which tends to minimize person-to-person subjectivity.

A physiological fluid tested in the present method is GCF, tongue scrapings, tongue biofilm, gumline biofilm, saliva, or breath, or a combination of a plurality of these fluids.

In one embodiment of the method of the present invention, a filter paper strip is impregnated with the reagent mixture by contacting the strip with the reagent solution, and allowing excess solvent to evaporate, to form an impregnated test strip. Saliva is then expectorated by a subject onto the impregnated test strip. Reaction is allowed to proceed in and on the impregnated test strip. After a fixed period of time, the concentration of thiol compounds is determined by comparison of the color developed on the surface of the impregnated test strip against a standard such as a scaled color chart.

In one embodiment, a test stick is used in a direct contact application. In this embodiment, a test stick is used that contains a porous pad at one end of the stick, wherein the pad is impregnated with the test solution. The test solution in certain embodiments has been dried, allowing excess solvent to evaporate. The pad is placed in direct contact with the sample (e.g., saliva). After a period of time (e.g., 5-10 seconds), the pad is examined to determine the development of color, or a change in color.

In another embodiment, the test strip contains a comparator (i.e., internal control), adjacent to the detection pad. In one embodiment, reactive region and comparator regions of the unused test strip are of the same color. When these two regions of the test strip are placed in contact with the sample, they initially turn a different color from the unused test strip (i.e., the color they both acquire following hydration by the sample). After a period of time, the color of the reactive region diverges from the comparator region, with the intensity being indicative of the concentration of thiol compounds (e.g., as shown in FIG. 2A).

In another embodiment, the detection and comparator areas may initially have different colorations. The reactive pad becomes progressively more like comparator at higher concentration of thiols, and may surpass the cut-off intensity (e.g., as shown in FIG. 2B).

In another direct contact method embodiment, the strip contains three different regions: a comparator showing starting color, a comparator showing a cut-off (diagnostic) color, and a reactive region (FIG. 2C). The reactive region color diverges from starting (upper) color and converges with comparator (lower) as thiol levels increase. In such a case, an observer or an electronic device comparing the various regions makes a determination as to whether the reactive region (e.g., center pad) is more like the starting color (e.g., upper pad), or the comparator color (e.g., lower pad).

In another direct contact method embodiment, the strip contains two different regions: a reactive pad (top) starts out with light blue coloration; becomes progressively greener at higher concentrations of thiols (e.g., as shown in FIG. 2D). Coloration may meet or exceed the color or a comparator (below the pad). This is similar to the format shown in FIG. 2B, except that the positions of the detection and comparator pads have been switched.

In certain embodiments, different indicator colors are used, and/or different shapes are used (e.g., FIGS. 3A-3E).

Test Kit.

The present invention provides a test kit useful for the detection of thiol compounds. The kits include a reagent solution and/or the detection device described above.

The invention will now be further illustrated by the following non-limiting Further Examples.

Further Example 1

Reagent solution was formulated as follows:
Buffer (sodium phosphate, USP)—100 mM, pH 7.0
DTNB, 100 mg/L
Glycerol (USP), 0.5% by volume
xylitol (food/pharma grade), 4% by weight Further Example 2

Reagent solution was formulated as follows:

| Component and amount (for 1 L of solution) | |
| --- | --- |
| Deionized Water (DI H2O; suitable for ingestion) | ~800 mL + Q.S. to 1 L |
| Disodium phosphate heptahydrate, USP | 3.093 g (3.060-3.120 g) |
| Sodium phosphate, monobasic, USP | 1.015 g (1.010-1.020 g) |
| glycerol, USP | 5.0 mL (4.9-5.1 mL) |
| Xylitol, food/pharma grade | 40.0 g (39.6-40.4 g) |
| DTNB | 0.100 g (0.099-0.101 g) |
| 70% Isopropyl alc., (or USP grade IPA, diluted to 70%) | 100 mL (optional) |

The reagent solution was then filtered using a PES filter (0.2 micron pore size). Strips made with 50 or 100 mg DTNB/L solution were found to be reasonably suitable for a white pad, since that level of DTNB imparts little if any noticeable color to the pad, upon drying.

Further Example 3

It is known in the art that thiol compounds accumulate in fluid associated with spoiled meat. Accordingly, an article according to the invention is useful for the detection of elevated thiol levels associated with spoiled meat.

Further Example 4

It is known in the art that thiol compounds accumulate in fluid associated with degraded wallboard product, which contains calcium sulfate and is subject to degradation by sulfate-reducing bacteria. Accordingly, an article according to the invention is useful for the detection of elevated thiol levels associated with degraded wallboard products.

Further Example 5

Various further aspects of the invention are disclosed in the substance of the following presentation, in which the thiol detection reagent comprised a detection reagent according to Aspect 7 of the present invention.

Rapid Method for Detecting/Estimating Dissolved Oral Thiols

Objectives:

Oral halitosis and periodontal diseases very often involve the microbial production of Volatile Sulfur Compounds (VSCs), primarily hydrogen sulfide and methyl mercaptan. Historically, efforts have focused on detecting their presence in exhaled breath, rather than within microbial biofilms. Our objective was to develop test strips targeting dissolved thiols, which provide rapid, visual results, are easy to use, and are non-irritating to oral tissues.

Methods:

We screened various materials for their ability to provide visually discernable responses to dissolved thiols, after pre-treatment with a thiol detector compound. The propensity of the dried detection reagent to leach from the pad was estimated spectrophotometrically, by challenging rinse-fluid with added thiol. Prototype test strips were placed into a stability study in order to estimate shelf life. Irritancy testing was performed by an independent lab. Finally, we varied the concentration of the detection reagent, to determine if different "cut-off" result colorations could be achieved.

Results:

A porous pad material was identified, which had good physical characteristics and was compatible with the thiol detection reagent and its chromogenic product. Once dried onto the pad, the reagent showed a low propensity to leach upon rehydration, maintained good spectral responses, and showed reasonable stability over time. Pad treatment reagent was found to be non-irritating to cultured gingival tissue cells, when compared to standard oral care products. Finally, by raising or lowering the reagent concentration (amount of detector in the pad), we found we could manipulate the plateau coloration of the test.

Conclusions:

Our results suggest test strips employing this technology might be useful as aids in detecting causative agents of halitosis and periodontal diseases.

Our general approach in this endeavor was to exploit the qualities and abilities of a thiol detection reagent ("TDR"), to detect dissolved sulfur compounds relevant to oral malodor and periodontal diseases, and to do so using a dry-chemistry format. Certain design aspects and capabilities of that format are presented here.

Background

Oral malodor (halitosis) and chronic periodontal disease are commonly characterized by the presence of bacteria, either on the tongue dorsum or within the sulcus, between the tooth and gingival tissue, respectively. Many gram-negative anaerobic bacteria inhabiting these tongue and gingival biofilms, as they metabolize proteins bearing sulfur-containing amino acids, have the ability to remove the terminal sulfur-containing groups from cysteine and methionine, to produce hydrogen sulfide and methyl mercaptan, respectively.

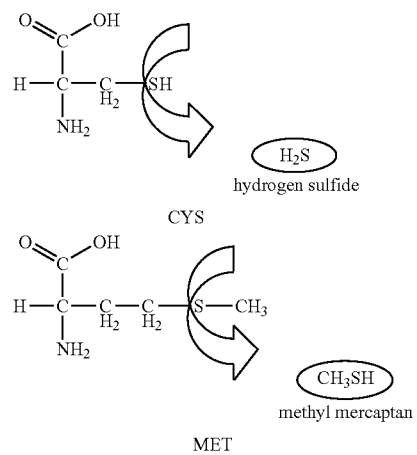

At body temperature, the bulk of the hydrogen sulfide and methyl mercaptan will volatilize, rather than remain dissolved in the aqueous milieu. As they enter the gas phase, they can be carried from the mouth by exhaled breath. Although other volatile compounds (containing sulfur or not containing sulfur) can contribute to oral halitosis, typically volatile sulfur compounds (VSC) are responsible, and among VSCs, these two compounds are thought to be the major contributors.

A great deal of research has been undertaken to identify and quantify the concentrations of these (exhaled) gases. Organoleptic assessment, often considered the gold standard for 'measuring' halitosis, requires training and calibration, and is not always easily accessible.

Instruments capable of quantifying exhaled gases include the Halimeter (Interscan Corporation) and OralChroma (Abilit). The Halimeter measures VSCs, though not other types of malodorous compounds. The Halimeter, however cannot discriminate between VSCs contributing to halitosis and those which do not. The OralChroma is a specialized gas chromatograph, which was designed to quantify the three most often encountered VSCs: hydrogen sulfide; methyl mercaptan; and dimethyl sulfide. Dimethyl sulfide has been shown to be present not in oral halitosis, but in other disease states. OralChroma only identifies and quantifies these three gases, so while it too lacks the ability to detect contributors to 'non-VSC' halitosis, it does specifically detect and quantify the primary VSC contributors, thereby providing better diagnostic information. This instrument however, is costly and likely not in wide use.

Methods

Screening Pad Materials

Various porous, absorbent materials were obtained and screened for their suitability for use as a sample pad. The desired material had to have certain inherent qualities, as well as achieve certain performance characteristics. Among these were the following:

provide acceptable color saturation or color shade change, from initial to final coloration
reach its plateau (final) coloration quickly
maintain the plateau coloration for a reasonable length of time
possess sufficient thickness and durability (manufacturability)
have a low-gloss appearance
achieve uniform distribution of TDR upon drying
provide sufficient capacity for the reagent and the biological (oral fluid) sample
achieve uniform and non-migrating distribution of TDR upon rehydration [by sample]
absorb sample as quickly and as evenly as possible
exhibit biocompatibility with oral tissues; minimal shedding of particulates
adhere to plastic (support) backing A number of cellulose and non-cellulose based papers, glass fiber materials, and synthetic materials were examined. A few of these (proving potentially useful) were chosen and ranked primarily on their ability to show suitable coloration, and secondarily on the basis of biocompatibility and color migration characteristics.

Leaching of Reagent from Pad

As part of the argument that the pad, once treated with TDR, would not be irritating to oral tissues, we demonstrated that in the time frame for use (oral tissue contact for a few seconds at most), TDR did not leach to a significant extent from the pad. This was accomplished by first attempting to rinse it from the dried pad, then challenging the rinse fluid with thiol, and back-calculating the percentage released to the solution, based on the total TDR within the pad.

Irritancy Testing (in vitro)

As a second approach to irritation testing, we sent the solution containing the TDR to an independent laboratory, for in vitro testing using cell lines established for this purpose. Using strict quality control procedures and comparing to existing oral care formulations, an indication of the relative irritancy for the reagent solution could be determined.

Stability Study (Feasibility Stage)

In order to demonstrate stability of feasibility-phase prototypes, short-term stability studies were undertaken, employing both real-time and accelerated (storage at higher temperature) aging. Such studies can either raise concerns early-on in the development process, or provide a sense of confidence that subsequent prototypes (and ultimately, the manufactured products themselves), will exhibit the stability necessary for suitably long shelf-lives. Strips were packaged and stored at various temperatures, then challenged with standard thiol solutions at predetermined time points during the course of the experiment. From the results, both realistic and conservative estimates of stability can be derived, using the Arrhenius model (Anderson, G., and M. Scott (1991) *Clin Chem* 37:398-402).

Limiting the Reagent

To determine if different plateau (final) test colorations could be achieved, we reduced the concentration of the TDR concentration, so it would be limiting. An ability to dictate the final color of the test would demonstrate that similar types of devices could be devised, which exhibit different cut-off concentrations.

Results

Screening Pad Materials

Interestingly, the chromogenic reaction product (of TDR+ thiol) often migrated through the pad matrices, from the application point of the thiol solution. Typically, freshly-made aqueous thiol dilutions are made, just prior to testing, using 2-mercaptoethanol (2-ME) as a standard thiol. These were pipetted onto the dried pad, and the behavior of the color-change was monitored over time. That there was migration of color at the front of the liquid suggested the dried TDR was likely free to be carried by the liquid upon rehydration. Such materials would not make good pads, since the desired output is a uniform field (of color change).

Other materials looked promising, in that the color change was adequately visible and non-migrating. However, the fibers in some of these pads were relatively loose, (and likely to prove problematic in terms of biocompatibility). So, while meeting criteria for inertness and visibility of color change, they would need to be isolated from direct oral contact in order to render them usable.

Figure 11:
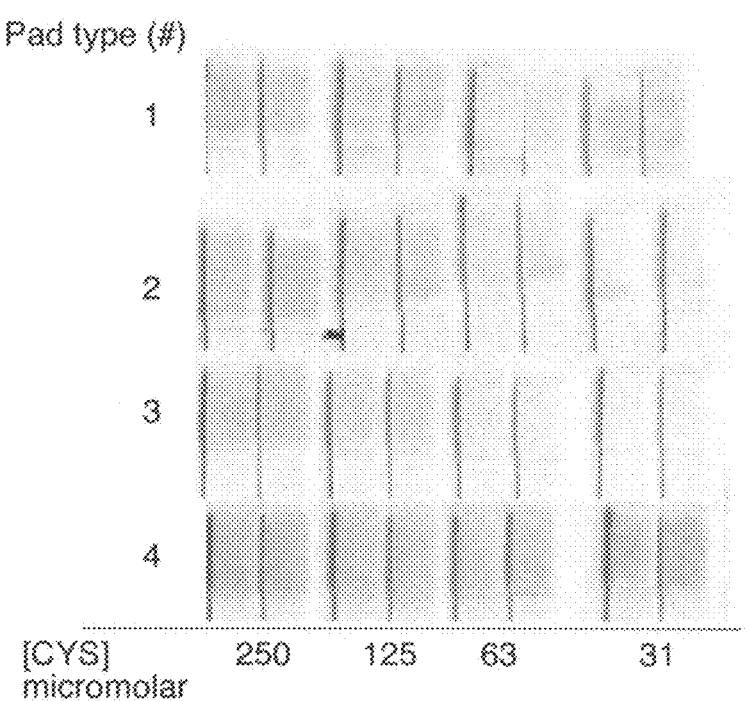
FIG. 11 shows the results of materials used in a short-term stability study, treated with a prototype TDR solution.

We did achieve good results, with materials that provided what we believe were the best combination of signal-to-noise, biocompatibility, and visibility of color change. In addition, these could be provided in custom thicknesses, were easily handled, sufficiently hydrophilic, and adaptable to both manual and automated manufacturing situations. Five materials were chosen for a short-term stability study, treated with a prototype TDR solution, and stored at room temperature and at 37° C. for several weeks. After 6 weeks these TDR-treated materials were challenged using cysteine solutions (250 µM and lower); results for four of the five were photographed, and are shown in FIG. 11. Pad materials stored at ambient temperature are on the left in each pair; those stored at 37° C. are on the right. The pad material numbered 4 showed the best overall color intensities, color retention, and sensitivity across the thiol concentration range.

Leaching of Reagent from Pad

Figure 12:
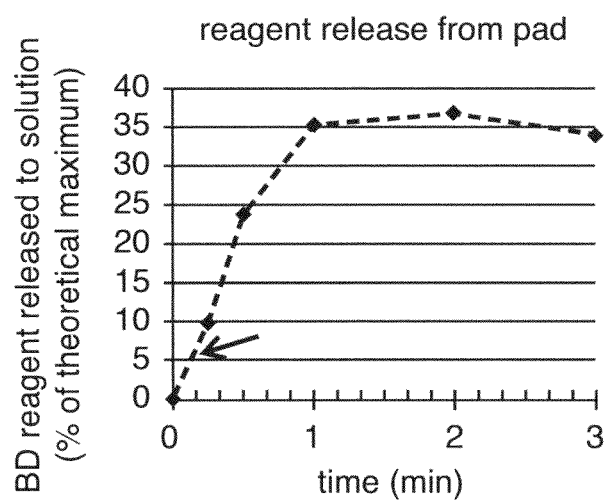
FIG. 12 shows the amount of reagent released from pad.

After pads were agitated in 250 μL water (in cuvettes) for times up to 3 minutes, rehydrated TDR that leached from the pads into solution was challenged with 25 μL of 1 mM cysteine. The yellow color generated was read by spectrophotometry at t=30 sec. These signals were expressed as percentages of the maximum theoretical value (i.e., based on signal generated by using the amount of liquid TDR dried onto each pad). FIG. 12 demonstrates that only ~⅓ the maximum theoretical amount exits the pad upon hydration; and that level of leaching is reached after approximately one minute of agitation within the cuvette. The oral contact time for the pad however, is only about 5 seconds. One can see even at 10 sec (arrow in figure), that the amount of reagent exiting the pad is around 5% of the total, and this assumes agitation in a relatively large fluid volume, rather than a brief surface contact with mucosal tissue (during which fluid movement would be into, rather than out of, the pad).

Irritancy Testing (in vitro)

Testing was undertaken by the MatTek Corporation (Ashland, Mass.). Liquid TDR was sent to MatTek, and assayed in their standard tested algorithm, using a cell culture system, "EpiOral" ORL-200. Irritation potential was assessed as "ET-50", defined as the time at which the cultured cell mortality reaches 50%. The test results are shown in Table 1, below.

TABLE 1

|  | time (hr) | surviving cells (%) | error | ET-50 (hr) |
| --- | --- | --- | --- | --- |
| detection reagent | 4 | 120.4 | 3.6 | >24 |
|  | 18 | 106.9 | 5.9 |  |
|  | 24 | 98.6 | 0.7 |  |

TABLE 1-continued

|  | time (hr) | surviving cells (%) | error | ET-50 (hr) |
| --- | --- | --- | --- | --- |
| children's toothpaste | 4 | — | — | 12.4 |
|  | 18 | 36.6 | 6.5 |  |
|  | 24 | 26.2 | 0.8 |  |
| teeth whitener | 4 | 84.2 | 7.1 | 15.2 |
|  | 18 | 45.6 | 20.7 |  |
|  | 24 | 58.2 | 14.7 |  |

At the 24 hour time point, nearly 100% of the cells in the tissue were still viable, so ET-50 is then defined as >24 hr. For the toothpaste and whitener instances, half the cells had been killed at about 12 and 15 hours, respectively.

Stability Study

The stability study results reported in the table (FIG. 14) provide both "realistic" ($Q_{10}$=3.00) and "conservative" ($Q_{10}$=2.00) estimates of stability. The prototype pads in this study contained about ¼ the amount of the active TDR present in the MatTek study (immediately above), and were stored as test strips, singly, in sealed foil pouches (no desiccant). Appropriate reactivity was also seen on a subset of tests stored at 45° C., and tested fully at the end of the experiment. In this case, the "realistic" estimate of stability was 2.4 years ($Q_{10}$=3.00), and the "conservative" estimate was 1.13 years ($Q_{10}$=2.00).

---

Calculation of Degradation Rates at a Given Temperature
Based on Product Degradation at Higher Temperatures
where product with activation energy of Ea is stored at temperature T1 and exhibits a degradation rate k1;
expected degradation rate is calculated (k2) for when product is stored at temperature T2

Realistic Estimate ($Q_{10}$ = 3)

Given:
k1 = 1 sec(-1)*  $Q_{10}$ = 3.00
Ea = 18.7 kcal/mole
R = 1.9871 calories degrees K(-1) mole   T1 (K) = 310° K.
T1 (° C.) = 37 deg. C.   T2 (K) = 295° K.
T2 (° C.) = 22 deg. C.

Then:
k2 = 0.21361M(-1)sec(-1)

Which Means
88 day(s) at    37° C. is equivalent to    411.96 days or
                                           13.53 months or   } at    22° C.
                                           1.128 years Conservative Estimate ($Q_{10}$ = 2)

Given:
k1 = 1 sec(-1)*  $Q_{10}$ = 2.00
Ea = 12.55 kcal/mole
R = 1.9871 calories degrees K(-1) mole   T1 (K) = 310 deg. K
T1 (° C.) = 37 deg. C.   T2 (K) = 295 deg. K
T2 (° C.) = 22 deg. C.

Then:
k2 = 0.3549M(-1)sec(-1)

Which Means
88 day(s) at    37° C. is equivalent to    247.96 days or
                                           8.15 months or   } at    22° C.
                                           0.679 years Based on:
$\ln(k2/k1) = (-Ea/R)*((1/T2) - (1/T1))$ Note:
$E_a \approx 6.15(Q_{10}) + 0.25$ Limiting TDR By limiting the TDR in the pad, one should be able to dictate a "maximum" color change, even for thiol concentrations which would otherwise produce additional color change, given a sufficient amount of TDR.

Figure 13:
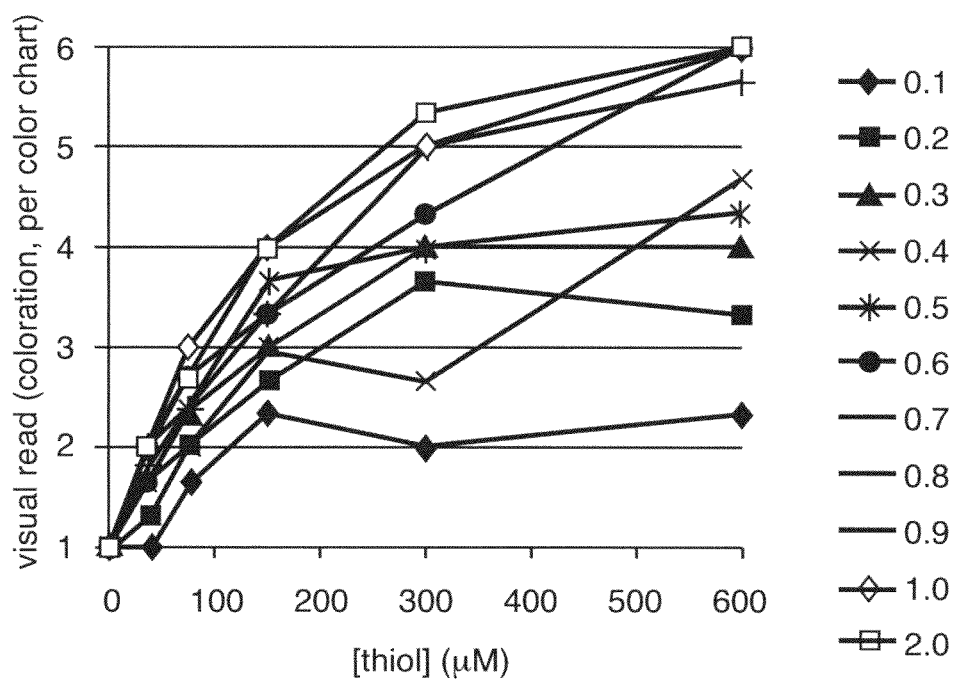
FIG. 13 shows a graph of the level of signal (visual output) as compared to the amount of TDR present.

FIG. 13 shows that, when TDR is varied over a 20-fold range (per the legend along the right edge of the graph), the final coloration noted also varies, based upon numbered colors (y-axis) read visually from a color 'comparator' chart. One sees the general rise in final signal (visual output) as the amount of TDR increases, which is what would be expected based on stoichiometry.

Discussion and Conclusions

Based on the selected design aspects presented here, we identified candidate materials to serve as a pad (specimen collection and reaction stage) for a "dissolved thiol" oral fluid test. Subsequent to the initial pad screening studies, additional pad materials were examined, which exhibited features superior even to pad type #4 (not shown).

The TDR remains within the pad upon rehydration (i.e., during the oral sample collection process, requiring no more than a few seconds), and seems to be quite stable once it has been dried. Given these characteristics, and the relatively low amounts of TDR needed per test, we were encouraged to find that the TDR in liquid format was non-irritating to a cultured cell system. Further safety-related tests (formal cytotoxicity, irritancy, and sensitization testing, of complete tests in the planned format) are being planned, to support the biocompatibility testing done to date.

The stability study data suggest tests based on this type of dried-down reagent should have shelf lives appropriate for marketable products, under normal storage conditions.

Further Example 6

An article according to the invention is useful for screening for risks of complications of chronic disease, including cardiovascular disease. It is known in the art that persons with cardiovascular disease who also suffer from periodontitis are at higher risk of morbidity and mortality than persons with cardiovascular disease who do not suffer from periodontitis. Accordingly, an article according to the invention is useful in the screening of populations of persons with cardiovascular disease for those who, on account of their also suffering from periodontitis, are at a relatively high risk of morbidity and mortality. In particular, a first sample of oral fluid from a first subject with cardiovascular disease is contacted with a matrix of an article according to the invention, and a first and relatively more intense signal indicating a relatively higher concentration of thiol compounds in the first sample is observed. A second sample of oral fluid from a second subject with cardiovascular disease is contacted with a substantially similar matrix of a substantially similar article according to the invention, and a relatively less intense signal indicating a relatively lower concentration of thiol compounds in the second sample is observed. It is concluded that the first subject is at relatively higher risk of morbidity and mortality than the second subject.

Further Example 7

An article according to the invention is useful for screening for risks of complications of chronic disease, including Type II diabetes. It is known in the art that persons with Type II diabetes who also suffer from periodontitis are at higher risk of morbidity and mortality than persons with Type II diabetes who do not suffer from periodontitis. Accordingly, an article according to the invention is useful in the screening of populations of persons with Type II diabetes for those who, on account of their also suffering from periodontitis, are at a relatively high risk of morbidity and mortality. In particular, a first sample of oral fluid from a first subject with Type II diabetes is contacted with a matrix of an article according to the invention, and a first and relatively more intense signal indicating a relatively higher concentration of thiol compounds in the first sample is observed. A second sample of oral fluid from a second subject with Type II diabetes is contacted with a substantially similar matrix of a substantially similar article according to the invention, and a relatively less intense signal indicating a relatively lower concentration of thiol compounds in the second sample is observed. It is concluded that the first subject is at relatively higher risk of morbidity and mortality than the second subject.

Further Example 8

An article according to the invention is useful for screening for risks of preterm labor and/or delivery in pregnant subjects. It is known in the art that pregnant women who suffer from periodontitis are at higher risk of preterm labor and/or delivery than pregnant women who do not suffer from periodontitis. Accordingly, an article according to the invention is useful in the screening of populations of pregnant women for those who, on account of their suffering from periodontitis, are at a relatively high risk of preterm labor and/or delivery. In particular, a first sample of oral fluid from a first pregnant subject is contacted with a matrix of an article according to the invention, and a first and relatively more intense signal indicating a relatively higher concentration of thiol compounds in the first sample is observed. A second sample of oral fluid from a second pregnant subject is contacted with a substantially similar matrix of a substantially similar article according to the invention, and a relatively less intense signal indicating a relatively lower concentration of thiol compounds in the second sample is observed. It is concluded that the first subject is at relatively higher risk of preterm labor and/or delivery than the second subject.

Further Example 9

An article according to the invention is useful for detecting periodontal disease activity in a mammalian subject. It is known in the art that periodontal disease, and in particular periodontitis, is nonmonotonic in its progression. Higher levels of thiols are detected at times of greater disease activity than are detected at times of lesser disease activity. Accordingly, an article according to the invention is useful in the detection of periodontal disease activity. At a first time-point, a first sample of oral fluid from a subject is contacted with a matrix of an article according to the invention, and a first and relatively more intense signal indicating a relatively higher concentration of thiol compounds in the first sample is observed. At a second time-point, a second sample of oral fluid from the subject is contacted with a substantially similar matrix of a substantially similar article according to the invention, and a relatively less intense signal indicating a relatively lower concentration of thiol compounds in the second sample is observed. It is concluded that periodontal disease activity is higher in the subject at the first time-point than at the second time-point.

Further Example 10

An article according to the invention is useful for detecting acute periodontitis in a mammalian subject when compared against a background in that same subject of a lack of acute periodontitis. It is known in the art that, in a particular subject, higher levels of thiols are detected at times of acute periodontitis than are detected at times in which acute periodontitis is absent. Accordingly, an article according to the invention is useful in the detection of acute periodontitis. At a first time-point, a first sample of oral fluid from a subject is contacted with a matrix of an article according to the invention, and a first and relatively less intense signal indicating a concentration of 50 micromolar thiol compounds in the first sample is observed. At a second time-point, a second sample of oral fluid from the subject is contacted with a substantially similar matrix of a substantially similar article according to the invention, and a relatively more intense signal indicating a concentration of 500 micromolar thiol compounds in the second sample is observed. It is concluded that the subject is suffering from acute periodontitis at the second time-point.

Further Example 11

An article according to the invention is useful for determining efficacy of treatment in a mammalian subject being treated for periodontitis. It is known in the art that, when periodontitis has been effectively treated, the level of thiol compounds in oral fluids is decreased with respect to the level of thiol compounds in oral fluids immediately prior to treatment. Accordingly, an article according to the invention is useful in the determination of efficacy of treatment. At a first time-point, immediately prior to the initiation of treatment, a first sample of oral fluid from a subject is contacted with a matrix of an article according to the invention, and a first and relatively more intense signal indicating a concentration of 750 micromolar thiol compounds in the first sample is observed. At a second time-point, two weeks following the initiation of treatment, a second sample of oral fluid from the subject is contacted with a substantially similar matrix of a substantially similar article according to the invention, and a relatively less intense signal indicating a concentration of 120 micromolar thiol compounds in the second sample is observed. It is concluded that treatment has been efficacious.

Further Example 12

An article according to the invention is useful for determining lack of efficacy of treatment in a mammalian subject being treated for periodontitis. It is known in the art that, when periodontitis has not been effectively treated, the level of thiol compounds in oral fluids is not decreased with respect to the level of thiol compounds in oral fluids immediately prior to treatment. Accordingly, an article according to the invention is useful in the determination of lack of efficacy of treatment. At a first time-point, immediately prior to the initiation of treatment, a first sample of oral fluid from a subject is contacted with a matrix of an article according to the invention, and a first signal indicating a concentration of 750 micromolar thiol compounds in the first sample is observed. At a second time-point, two weeks following the initiation of treatment, a second sample of oral fluid from the subject is contacted with a substantially similar matrix of a substantially similar article according to the invention, and a signal indicating a concentration of 750 micromolar thiol compounds in the second sample is observed. It is concluded that treatment has not been efficacious.

Further Example 13

An article according to the invention is useful for monitoring periodontal disease activity in a mammalian subject. It is known in the art that periodontal disease, and in particular periodontitis, is nonmonotonic in its progression. Higher levels of thiols are detected at times of greater disease activity than are detected at times of lesser disease activity. Accordingly, an article according to the invention is useful in the monitoring of periodontal disease activity. At a first time-point, a first sample of oral fluid from a subject is contacted with a matrix of an article according to the invention, and a first and relatively more intense signal indicating a relatively higher concentration of thiol compounds in the first sample is observed. At a second time-point, a second sample of oral fluid from the subject is contacted with a substantially similar matrix of a substantially similar article according to the invention, and a relatively less intense signal indicating a relatively lower concentration of thiol compounds in the second sample is observed. It is concluded that periodontal disease activity has decreased in the subject from the first time-point to the second time-point.

Further Example 14

An article according to the invention is useful for detecting infection with pathogenic sulfate-reducing bacteria at a site in or on a subject. It is known in the art that pathogenic sulfate-reducing bacteria produce thiol compounds as metabolic end-products. Higher levels of thiols are detected in a fluid from a pathogenic sulfate-reducing-bacteria-infected site than are detected in a fluid from the same site when the site is not infected with sulfate-reducing bacteria. Accordingly, an article according to the invention is useful in the detection of infection with pathogenic sulfate-reducing bacteria. At a first time-point, a first sample of oral fluid from a site in or on a subject is contacted with a matrix of an article according to the invention, and a first and relatively less intense signal indicating a concentration of 25 micromolar thiol compounds in the first sample is observed. At a second time-point, a second sample of oral fluid from the same site in or on the subject is contacted with a substantially similar matrix of a substantially similar article according to the invention, and a relatively more intense signal indicating a concentration of 1500 micromolar thiol compounds in the second sample is observed. It is concluded that the subject is suffering from infection with pathogenic sulfate-reducing bacteria at or near the site.

Further Example 15

The person skilled in the art will appreciate that a so-called sulfhydryl reagent may be used as a component of a detection reagent according to the invention, that a pharmaceutically acceptable buffer may be used in place of phosphate buffer, that a pharmaceutically or cosmetically acceptable humectant or emollient may be used in place of glycerol and/or xylitol, and so forth. For this reason, many equivalents to what is described in haec verba in the above description will be apparent to one skilled in the art to which the present invention pertains.

Further Example 16

It will also be readily apparent that an apparatus according to the invention is useful for dental practitioners wishing to contain costs by spending less time per patient. That is, for such a practitioner to be able to determine within 10 seconds the state of that practitioner's patient's oral health is to be desired when compared to the tens of minutes or longer required for alternative diagnostic methods. Moreover, because periodontitis is associated with systemic disease morbidity, such as with diabetes, cardiovascular disease, and preterm delivery, it will be apparent to the person skilled in the art that the present invention provides a method for screening for the presence of any one or more of these disease states or health risk factors. Because per patient per month costs are higher for healthcare reimbursement companies reimbursing healthcare costs for patients having one or more of these disease states when compared to costs of healthy individuals, it is apparent that the present invention provides a method for containing per patient per month reimbursement costs by screening for early diagnosis of periodontitis.

Further Example 17

Establishment of reference values. In connection with the invention, a reference value relates to a value associated with a concentration of thiol compounds. In connection with the invention, a reference value can be established in any of a number of ways. For example, a signal derived from a first known concentration of a model thiol compound can be measured. In particular, a sample of a fluid containing the first known concentration of the model thiol compound can be contacted with a matrix comprising an amount of a detection reagent, thereby forming a first thiol-standard-contacted matrix providing a first signal. Likewise, a signal derived from a second known concentration of the model thiol compound can be measured. In particular, a sample of a fluid containing the second known concentration of the model thiol compound can be contacted with a substantially identical matrix comprising a substantially identical amount of the detection reagent, thereby forming a second thiol-standard-contacted matrix providing a second signal. If, for example, the first signal and the second signal can each be perceived by eye as, respectively, a first color-intensity and a second color-intensity, the first color-intensity and the second color-intensity can each be depicted, for example, respectively, as a first color-intensity "chip" or swatch and a second color-intensity "chip" or swatch. More generally, whether or not the first signal and the second signal are in the visible spectrum, the first signal and the second signal can be recorded. Accordingly, a sample of a fluid containing an unknown concentration of thiol compounds can be contacted with a substantially identical matrix comprising a substantially identical amount of the detection reagent, thereby forming an unknown-contacted matrix providing a third signal, and the third signal can be compared to the first signal and the second signal for determination of which of the two signals the third signal more closely approximates. As will be apparent to a person skilled in the diagnostic test strip and chemical arts, a signal provided by each of an arbitrarily large number of concentrations of a model thiol compound can be detected and recorded, for establishment of an arbitrarily large number of reference values. The appropriate manner of interpolation and/or establishment of standard curves and/or determination of the limits of dynamic range on the basis of such reference values, as well as their appropriate statistical treatment, will also be apparent to a person skilled in the diagnostic test strip and chemical arts. Any of a number of thiol compounds, for example, dithiothreitol or 2-mercaptoethanol, may be used as a model thiol compound. Similarly, for reference values related to a risk that a subject is suffering from a particular condition or malady, a reference value (indicative of lower risk of the condition or malady) may be established by determining, for example, a mean or median or range of signals provided by a plurality of matrices according to the invention each of which has been contacted with a sample of a physiological fluid obtained from a member of population that is not afflicted with the particular condition or malady, and another reference value (indicative of higher risk of the condition or malady) may be established by determining, in like manner, a mean or median range of signals provided by a plurality of matrices according to the invention each of which has been contacted with a sample of the physiological fluid obtained from a member of a population that is afflicted with the particular condition or malady.

The invention is yet further described in the following additional illustrative examples.

In a first additional illustrative example, it is found that 5-(2-aminoethyl)-dithio-2-nitrobenzoic acid is a useful thiol-detection reagent according to the invention. In this regard, for example, a stoichiometric amount of 5-(2-aminoethyl)-dithio-2-nitrobenzoic acid may be substituted for an amount of 5,5'-dithiobis-(2-nitrobenzoic acid), in whole or in part.

In a second additional illustrative example, it is found that an article according to the invention is useful for each of the following with respect to a condition detectable by sampling a fluid from a mammalian subject, and in particular a fluid from the oral cavity of a mammalian subject: screening for the condition; detecting the condition; diagnosing the condition; monitoring the condition; and/or serving as an aid and/or adjunct in screening for the condition, detecting the condition, diagnosing the condition, and/or monitoring the condition.

In a third additional illustrative example, a condition of a mammalian subject with respect to which condition an article according to the invention is useful in screening for the condition, detecting the condition, diagnosing the condition, monitoring the condition; and/or serving as an aid and/or adjunct in screening for the condition, detecting the condition, diagnosing the condition, and/or monitoring the condition includes any one or more of the following: periodontitis; gingivitis; halitosis; periodontal disease; periodontal disease activity; anaerobic microbial infection; being at increased risk of cardiovascular disease; being at increased risk of Type II diabetes; and/or being at increased risk of preterm delivery.

In a fourth additional illustrative example, an article according to the invention is useful in the following manner or any equivalent thereof. In one or a plurality of studies, for each of a plurality of mammalian subjects, a thiol concentration in a sample of fluid from the subject is determined, for example according to Aspect 13 above. Additionally, for each of the plurality of mammalian subjects, the subject's condition is determined, and, in particular, for example, the subject's condition with respect to any one or more of the conditions recited in the third additional illustrative example above. A database is assembled in which the thiol concentration thereby determined and the condition thereby determined are related one to another. A relationship between thiol concentration and condition is thereby established.

In a fifth additional illustrative example, the relationship established according to the fourth additional illustrative example above is that a higher thiol concentration is associated with a greater incidence and/or prevalence and/or risk of the condition.

In a sixth additional illustrative example, the relationship established according to the fourth additional illustrative example above is that a thiol concentration greater than or equal to a threshold concentration is associated with a meaningfully greater incidence and/or prevalence and/or risk of the condition.

In a seventh additional illustrative example, an article according to the invention is contacted with a sample of fluid from a subject and the thiol concentration in the sample is determined, for example according to Aspect 13 above. The thiol concentration in the sample is compared to the threshold concentration of the sixth additional illustrative example above. If the thiol concentration in the sample is greater than or equal to the threshold concentration, it is determined that the subject is at meaningful risk of having the condition.

In an eighth additional illustrative example, the condition according to the seventh additional illustrative example is periodontitis, and the threshold concentration is between about 150 micromolar and about 500 micromolar, or between about 155 micromolar and about 400 micromolar, or between about 160 micromolar and about 300 micromolar.

In a ninth additional illustrative example, the condition according to the seventh additional illustrative example is gingivitis, and the threshold concentration is between about 75 micromolar and about 300 micromolar, or between about 78 micromolar and about 200 micromolar, or between about 80 micromolar and about 150 micromolar.

In a tenth additional illustrative example, the condition according to the seventh additional illustrative example is halitosis, and the threshold concentration is between about 38 micromolar and about 100 micromolar, or between about 39 micromolar and about 90 micromolar, or between about 40 micromolar and about 80 micromolar.

In an eleventh additional illustrative example, the condition according to the seventh additional illustrative example is cardiovascular disease, and the threshold concentration is between about 150 micromolar and about 500 micromolar, or between about 155 micromolar and about 400 micromolar, or between about 160 micromolar and about 300 micromolar.

In a twelfth additional illustrative example, the condition according to the seventh additional illustrative example is Type II diabetes, and the threshold concentration is between about 150 micromolar and about 500 micromolar, or between about 155 micromolar and about 400 micromolar, or between about 160 micromolar and about 300 micromolar.

In a thirteenth additional illustrative example, the condition according to the seventh additional illustrative example is preterm delivery, and the threshold concentration is between about 150 micromolar and about 500 micromolar, or between about 155 micromolar and about 400 micromolar, or between about 160 micromolar and about 300 micromolar.

In a fourteenth additional illustrative example, the condition according to the seventh additional illustrative example is cardiovascular disease, and the threshold concentration is between about 75 micromolar and about 300 micromolar, or between about 78 micromolar and about 200 micromolar, or between about 80 micromolar and about 150 micromolar.

In a fifteenth additional illustrative example, the condition according to the seventh additional illustrative example is Type II diabetes, and the threshold concentration is between about 75 micromolar and about 300 micromolar, or between about 78 micromolar and about 200 micromolar, or between about 80 micromolar and about 150 micromolar.

In a sixteenth additional illustrative example, the condition according to the seventh additional illustrative example is preterm delivery, and the threshold concentration is between about 75 micromolar and about 300 micromolar, or between about 78 micromolar and about 200 micromolar, or between about 80 micromolar and about 150 micromolar.

In a seventeenth additional illustrative example, an article according to the invention is contacted at a site in the oral cavity to collect a sample of fluid from a subject according to the seventh additional illustrative example, and the condition according to the seventh additional illustrative example is any one or more of: periodontitis; gingivitis; periodontal disease; periodontal disease activity; and/or anaerobic microbial infection. In this seventeenth additional illustrative example, if the thiol concentration in the sample is greater than or equal to the threshold concentration, it is determined that the subject is at meaningful risk of having the condition at the site in the oral cavity at which the article has been contacted.

In an eighteenth additional illustrative example, an article according to the invention is contacted with a locus in the oral cavity to collect a sample of fluid from a subject according to the seventh additional illustrative example. In this eighteenth additional illustrative example, the locus in the oral cavity with which the article is contacted includes one or a plurality of: lower buccal gumline; lower buccal gumline between the incisors; lingual vestibule; tongue dorsum; left lower buccal gumline; and/or right lower buccal gumline. The thiol concentration in the sample is compared to the threshold concentration of the sixth additional illustrative example above. If the thiol concentration in the sample is greater than or equal to the threshold concentration, it is determined that the subject is at meaningful risk of having the condition.

Although the foregoing specification and examples fully disclose and enable the present invention, they are not intended to limit the scope of the invention, which is defined by the claims appended hereto. A person skilled in the art to which the invention pertains will recognize equivalents to what is disclosed in this application. Accordingly, the invention encompasses the scope of the appended claims and those in any patent claiming priority from and/or arising out of and making reference to this application, as well as any and all equivalents.

All publications, patents and patent applications are incorporated herein by reference. To the extent there is any conflict or inconsistency between the content of any such reference and the content of the teachings of this application apart from any such reference, the content of the teachings of this application apart from any such reference shall control. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A single-use disposable article for determining the concentration of thiol compounds in a sample of fluid, the article comprising:
   (a) a matrix comprising at least one absorbent material comprising a polyamide material, the matrix being capable of absorbing the sample;
   (b) an amount of a detection reagent, the amount of the detection reagent being capable of providing, during a period of time after at least a portion of the amount of the detection reagent has been contacted with at least a portion of the sample, a signal indicating the concentration of thiol compounds in the sample; and
   (c) a comparator region,
   wherein the detection reagent comprises 10 mg/L to 150 mg/L 5,5'-dithiobis-(2-nitrobenzoic acid) (DTNB), 20 mM to 150 mM imidazole or phosphate buffer, about 0.1 mM manganese chloride, 0.1% to 5.0% by volume glycerol, and 2% to 10% by weight xylitol.

2. The article of claim 1, wherein the detection reagent further comprises at least one of: 5-(2-aminoethyl)-dithio-2-nitrobenzoic acid; N,N'-bis (4-nitrobenzylidene)-4,4'-dithiodianiline; N,N'-bis (3-nitrobenzylidene)-4,4'-dithiodianiline; N,N'-bis (2-nitrobenzylidene)-4,4'-dithiodianiline; N,N'-bis (2,4-dinitrobenzylidene)-4,4'-dithiodianiline; or N,N'-bis (4-nitrocinnamalylidene)-4,4'-dithiodianiline.

3. A single-use disposable test strip for determining the concentration of thiol compounds in a sample of a fluid from a mammalian subject, the test strip comprising:
   (a) a matrix comprising at least one absorbent fiber material comprising a polyamide material, the matrix being capable of absorbing the sample;
   (b) an amount of a detection reagent comprising 10 mg/L to 150 mg/L 5,5'-dithiobis-(2-nitrobenzoic acid) (DTNB), 20 mM to 150 mM imidazole or phosphate buffer, about 0.1 mM manganese chloride, 0.1% to 5.0% by volume glycerol, and 2% to 10% by weight xylitol, the amount of the detection reagent being capable of providing, during a period of time after at least a portion of the amount of the detection reagent has been contacted with at least a portion of the sample, a signal indicating the concentration of thiol compounds in the sample; and
   (c) a comparator region.

4. The test strip of claim 3, wherein the detection reagent further comprises at least one of: 5-(2-aminoethyl)-dithio-2-nitrobenzoic acid; N,N'-bis (4-nitrobenzylidene)-4,4'-dithiodianiline; N,N'-bis (3-nitrobenzylidene)-4,4'-dithiodianiline; N,N'-bis (2-nitrobenzylidene)-4,4'-dithiodianiline; N,N'-bis (2,4-dinitrobenzylidene)-4,4'-dithiodianiline; or N,N'-bis (4-nitrocinnamalylidene)-4,4'-dithiodianiline.

5. The test strip of claim 3, wherein the period of time begins about one second after the at least a portion of the amount of the detection reagent has been contacted with the at least a portion of the sample and ends about ten minutes after the at least a portion of the amount of the detection reagent has been contacted with the at least a portion of the sample.

6. The test strip of claim 3, wherein the period of time begins about five seconds after the at least a portion of the amount of the detection reagent has been contacted with the at least a portion of the sample and ends about five minutes after the at least a portion of the amount of the detection reagent has been contacted with the at least a portion of the sample.

7. The test strip of claim 3, wherein the signal comprises an electromagnetic signal.

8. The test strip of claim 7, wherein the electromagnetic signal comprises a visible signal.

9. The test strip of claim 3, further comprising a humectant.

10. A single-use disposable test strip for determining the risk that a mammalian subject is suffering from a particular malady, the test strip comprising:
    (a) a matrix comprising at least one absorbent material comprising a polyamide material, the matrix being capable of absorbing a sample from the subject;
    (b) an amount of a detection reagent comprising 10 mg/L to 150 mg/L 5,5'-dithiobis-(2-nitrobenzoic acid) (DTNB), 20 mM to 150 mM imidazole or phosphate buffer, about 0.1 mM manganese chloride, 0.1% to 5.0% by volume glycerol, and 2% to 10% by weight xylitol, the amount of the detection reagent being capable of providing, during a period of time after at least a portion of the amount of the detection reagent has been contacted with at least a portion of the sample, a signal indicating the risk that the subject is suffering from the particular malady, and wherein
    the particular malady is at least one of: periodontitis, gingivitis, halitosis, cardiovascular disease, type II diabetes, or preterm delivery; and
    (c) a comparator region.

11. The test strip of claim 10, wherein the particular malady is periodontitis.

12. The test strip of claim 11, wherein the signal indicates that the concentration of thiol compounds in the sample is at least about 160 micromolar.

13. The test strip of claim 12, wherein the signal indicates that the concentration of thiol compounds in the sample is at least about 200 micromolar.

14. The test strip of claim 13, wherein the signal indicates that the concentration of thiol compounds in the sample is at least about 240 micromolar.

15. The test strip of claim 10, wherein the particular malady is gingivitis.

16. The test strip of claim 15, wherein the signal indicates that the concentration of thiol compounds in the sample is at least about 80 micromolar.

17. The test strip of claim 16, wherein the signal indicates that the concentration of thiol compounds in the sample is at least about 100 micromolar.

18. The test strip of claim 17, wherein the signal indicates that the concentration of thiol compounds in the sample is at least about 120 micromolar.

19. The test strip of claim 10, wherein the particular malady is halitosis.

20. The test strip of claim 19, wherein the signal indicates that the concentration of thiol compounds in the sample is at least about 40 micromolar.

21. The test strip of claim 20, wherein the signal indicates that the concentration of thiol compounds in the sample is at least about 50 micromolar.

22. The test strip of claim 21, wherein the signal indicates that the concentration of thiol compounds in the sample is at least about 60 micromolar.

23. The test strip of claim 10, wherein the particular malady is cardiovascular disease.

24. The test strip of claim 10, wherein the particular malady is type II diabetes.

25. The test strip of claim 10, wherein the particular malady is preterm delivery.

26. The test strip of claim 10, further comprising a humectant.

27. The article of claim 1, wherein the glycerol is present at a concentration of about 0.5% by volume.

28. The article of claim 1, wherein the xylitol is present at a concentration of about 4% by weight.

29. A single-use disposable article for determining the concentration of thiol compounds in a sample of fluid, the article comprising:
   (a) a matrix comprising at least one absorbent material comprising a polyamide material, the matrix being capable of absorbing the sample;
   (b) an amount of a detection reagent, the amount of the detection reagent being capable of providing, during a period of time after at least a portion of the amount of the detection reagent has been contacted with at least a portion of the sample, a signal indicating the concentration of thiol compounds in the sample; and
   (c) a comparator region,
      further comprising a flavoring or scent.

30. A single-use disposable article for determining the concentration of thiol compounds in a sample of fluid, the article comprising:
   (a) a matrix comprising at least one absorbent material comprising a polyamide material, the matrix being capable of absorbing the sample;
   (b) an amount of a detection reagent, the amount of the detection reagent being capable of providing, during a period of time after at least a portion of the amount of the detection reagent has been contacted with at least a portion of the sample, a signal indicating the concentration of thiol compounds in the sample; and
   (c) a comparator region,
      wherein the dried detection reagent is stable for more than one year at room temperature.

31. A single-use disposable article for determining the concentration of thiol compounds in a sample of fluid, the article comprising:
   (a) a matrix comprising at least one absorbent material, the matrix being capable of absorbing the sample;
   (b) an amount of a detection reagent comprising 10 mg/L to 150 mg/L 5,5'-dithiobis-(2-nitrobenzoic acid) (DTNB), 20 mM to 150 mM imidazole or phosphate buffer, about 0.1 mM manganese chloride, 0.1% to 5.0% by volume glycerol, and 2% to 10% by weight xylitol, the amount of the detection reagent being capable of providing, during a period of time after at least a portion of the amount of the detection reagent has been contacted with at least a portion of the sample, a signal indicating the concentration of thiol compounds in the sample; and
   (c) a comparator region.

\* \* \* \* \*